(12) United States Patent
Di Tullio et al.

(10) Patent No.: US 11,707,254 B2
(45) Date of Patent: Jul. 25, 2023

(54) SPEED DETERMINATION FOR INTRALUMINAL ULTRASOUND IMAGING AND ASSOCIATED DEVICES, SYSTEMS, AND METHODS

(71) Applicant: VOLCANO CORPORATION, San Diego, CA (US)

(72) Inventors: Alessandra Di Tullio, Eindhoven (NL); Robin Lucia, San Diego, CA (US); Anuja Nair, San Diego, CA (US); Nikhil Sreedhar Rajguru, San Diego, CA (US); Yvonne Gillis, San Diego, CA (US)

(73) Assignee: PHILIPS IMAGE GUIDED THERAPY CORPORATION, San Diego (GA)

( * ) Notice: Subject to any disclaimer, the term of this patent is extended or adjusted under 35 U.S.C. 154(b) by 176 days.

(21) Appl. No.: 16/662,847

(22) Filed: Oct. 24, 2019

(65) Prior Publication Data
US 2020/0129143 A1    Apr. 30, 2020

Related U.S. Application Data

(60) Provisional application No. 62/751,185, filed on Oct. 26, 2018.

(51) Int. Cl.
*A61B 8/08* (2006.01)
*A61B 8/12* (2006.01)
*A61B 8/00* (2006.01)

(52) U.S. Cl.
CPC ............ *A61B 8/0891* (2013.01); *A61B 8/085* (2013.01); *A61B 8/12* (2013.01); *A61B 8/463* (2013.01)

(58) Field of Classification Search
CPC ......... A61B 8/0891; A61B 8/085; A61B 8/12; A61B 8/463; A61B 8/468; A61B 8/5223; A61B 8/461
See application file for complete search history.

(56) References Cited

U.S. PATENT DOCUMENTS

| 6,200,268 | B1 | 3/2001 | Vince |
| 6,381,350 | B1 | 4/2002 | Klingensmith |
| 6,398,755 | B1 | 6/2002 | Belef |
| 7,074,188 | B2 | 7/2006 | Nair |

(Continued)

FOREIGN PATENT DOCUMENTS

| WO | 2017102340 A1 | 6/2017 |
| WO | 2019175004 A1 | 9/2019 |

OTHER PUBLICATIONS

International Search Report & Written Opinion, dated Dec. 3, 2015.

*Primary Examiner* — Joseph M Santos Rodriguez
*Assistant Examiner* — Kaitlyn E Sebastian

(57) ABSTRACT

Disclosed is an intraluminal ultrasound imaging system, including a processor circuit in communication with an intraluminal ultrasound imaging catheter, and configured to receive a plurality of intraluminal ultrasound images obtained by the imaging catheter while the imaging catheter is moved through a body lumen of a patient. The processor circuit is further configured to determine a longitudinal translation speed of the imaging catheter based on the plurality of images and a known time interval between images, and display a speed indicator based on the longitudinal translation speed.

24 Claims, 16 Drawing Sheets

(56) References Cited

U.S. PATENT DOCUMENTS

| | | |
|---|---|---|
| 7,175,597 B2 | 2/2007 | Vince |
| 7,215,802 B2 | 5/2007 | Klingensmith |
| 7,359,554 B2 | 4/2008 | Klingensmith |
| 7,463,759 B2 | 12/2008 | Klingensmith |
| 7,846,101 B2 | 12/2010 | Eberle |
| 7,930,014 B2 | 4/2011 | Huennekens |
| 8,298,147 B2 | 10/2012 | Huenneken |
| 2006/0241465 A1* | 10/2006 | Huennekens .......... A61B 6/487 600/458 |
| 2011/0152882 A1* | 6/2011 | Wenderow ............ A61B 34/30 606/130 |
| 2015/0182190 A1 | 7/2015 | Hiltner |
| 2015/0196271 A1* | 7/2015 | Nair ...................... A61B 8/085 600/468 |
| 2016/0206267 A1* | 7/2016 | Shimizu ............... A61B 8/0891 |
| 2016/0235485 A1* | 8/2016 | Belohlavek ........... A61M 5/158 |
| 2017/0164922 A1* | 6/2017 | Waters .................. A61B 8/463 |
| 2017/0333000 A1* | 11/2017 | Nystrom ............... A61B 8/483 |
| 2018/0085095 A1* | 3/2018 | Hutchins .............. A61B 5/0066 |
| 2018/0360417 A1* | 12/2018 | Henneken ............. A61B 8/445 |
| 2019/0282182 A1 | 9/2019 | Scott |
| 2019/0282199 A1 | 9/2019 | Merritt |

* cited by examiner

SPEED DETERMINATION FOR INTRALUMINAL ULTRASOUND IMAGING AND ASSOCIATED DEVICES, SYSTEMS, AND METHODS

CROSS REFERENCE TO RELATED APPLICATIONS

This application claims priority to, and the benefit of, U.S. Provisional Patent Application No. 62/751,185, filed Oct. 26, 2018, which is incorporated by reference herein in its entirety.

TECHNICAL FIELD

The subject matter described herein relates to a system for medical imaging. In particular, the disclosed system provides a speed indicator to facilitate acquisition and display of peripheral intravascular ultrasound or IVUS images during a pullback procedure. This system has particular but not exclusive utility for diagnosis and treatment of vascular diseases.

BACKGROUND

Peripheral vascular procedures, such as angioplasty and stenting in peripheral venous (Inferior Vena Cava—IVC, iliac, femoral veins), IVC-filter retrieval, endovascular aneurysm repair (EVAR) and fenestrated endovasular repair (FEVAR) (and similar on the abdominal trait) atherectomy and thrombectomy are procedures where IVUS is used. Different diseases or medical procedures produce physical features with different size, structure, density, water content, and accessibility for imaging sensors. For example, a deep-vein thrombosis (DVT) produces a clot of blood cells, whereas post-thrombotic syndrome (PTS) produces webbing or other residual structural effects in a vessel that have similar composition to the vessel wall itself, and may thus be difficult to distinguish from the vessel wall. A stent is a dense (e.g., metallic) object that may be placed in a vessel or lumen to hold the vessel or lumen open to a particular diameter. A compression occurs when anatomical structures outside the vessel or lumen impinge on the vessel or lumen, constricting it.

In some cases, intraluminal imaging is carried out with an IVUS device including one or more ultrasound transducers. The IVUS device may be passed into the vessel and guided to the area to be imaged. The transducers emit ultrasonic energy and receive ultrasound echoes reflected from the vessel. The ultrasound echoes are processed to create an image of the vessel of interest. The image of the vessel of interest may include one or more lesions or blockages in the vessel. A stent may be placed within the vessel to treat these blockages and intraluminal imaging may be carried out to view the placement of the stent within the vessel. Other types of treatment include thrombectomy, ablation, angioplasty, pharmaceuticals, etc.

During a typical intraluminal imaging procedure (e.g., an IVUS pullback), an intraluminal imaging probe (e.g., an IVUS catheter for Peripheral Vascular interventions such as Philips Volcano: PV 0.014, PV 0.018, PV 0.035) is pulled or pushed manually by a clinician. A catheter can be attached to a pullback device or sled, which moves the catheter at a pre-defined speed. However, many doctors do not like to pullback devices because this requires an extra step to have to attach the catheter, and thus many find it easier to move the catheter manually. In particular, with phased array devices, there is no need at all to connect to a pullback device (so doctors prefer even more to move the catheter manually), whereas rotational IVUS device need to be connected to the pullback device, which also rotates the drive cable for imaging. Thus, for many applications the steadiness of the pullback speed depends on a physician's experience with the system, and care must be taken to move the probe at a speed (i.e., longitudinal translation velocity) that is consistent with high-resolution, high-detail, low-distortion, low-noise images. Pullback speeds that are too fast or too slow may degrade or distort image quality, and even brief pauses or direction reversals can result in confusing data. Less expert users may therefore have difficulty capturing consistent, high quality images.

The information included in this Background section of the specification, including any references cited herein and any description or discussion thereof, is included for technical reference purposes only and is not to be regarded as subject matter by which the scope of the disclosure is to be bound.

SUMMARY

Disclosed is a system for computing, displaying, and managing the speed of an intravascular imaging probe during an IVUS pullback or other intraluminal procedure that requires consistent probe movement speeds. For example, the present disclosure describes systems, devices, and methods for determining the movement speed of an intravascular probe during an IVUS intravascular procedure. According to at least one embodiment of the present disclosure, a system is provided for determining the pullback speed based on the content of the IVUS images themselves, and displaying the speed as navigation information to a clinician with respect to a desired range of speeds. This may be particularly useful during manually controlled intravascular procedures where a consistent probe speed (e.g., pullback speed) within a target range is desired. Determining pullback speed using the IVUS images themselves is different than determining speed by tracking the position of the catheter in externally captured images (e.g., fluoroscopic images), and in many cases requires fewer steps and less equipment. The system is hereinafter referred to as a pullback speed management system.

The pullback speed management system disclosed herein has particular, but not exclusive, utility for intraluminal ultrasound imaging procedures. The pullback speed management system includes an intraluminal ultrasound imaging system, including: a processor circuit configured for communication with an intraluminal ultrasound imaging catheter, where the processor circuit is configured to: receive a plurality of intraluminal ultrasound images obtained by the intraluminal ultrasound imaging catheter while the intraluminal ultrasound imaging catheter is moved through a body lumen of a patient; determine a longitudinal translation speed of the intraluminal ultrasound imaging catheter based on the plurality of intraluminal ultrasound images and a known time interval between each of plurality of intraluminal ultrasound images; and output, to a display in communication with the processor circuit, a screen display including a speed indicator based on the longitudinal translation speed. Other embodiments of this aspect include corresponding computer systems, apparatus, and computer programs recorded on one or more computer storage devices, each configured to perform the actions of the methods. A system of one or more computers can be configured to perform particular operations or actions by virtue of having software, firmware, hardware, or a combination of them installed on the system that in operation causes or cause the system to perform the actions. One or more computer programs can be configured to perform particular operations or actions by virtue of including instructions that, when executed by data processing apparatus, cause the apparatus to perform the actions.

Implementations may include one or more of the following features. The system where the processor circuit is configured to: update the longitudinal translation speed based on a further intraluminal ultrasound image is obtained while the intraluminal ultrasound imaging catheter is moved through the body lumen; and dynamically modify the speed indicator in the screen display such that the speed indicator indicates the longitudinal translation speed based on the further intraluminal ultrasound image. The system where the processor circuit is further configured to output, via the screen display, an intraluminal ultrasound image of the plurality of intraluminal ultrasound images, where the intraluminal ultrasound image is proximate to the speed indicator. The system where determining the longitudinal translation speed includes: identifying an anatomical feature or landmark in one or more of the plurality of intraluminal ultrasound images; and determining a change in the anatomical feature or landmark over the one or more of the plurality of intraluminal ultrasound images. The system where the processor circuit is configured to determine the longitudinal translation speed without tracking a position of the intraluminal ultrasound imaging catheter in an extraluminal image. The system where the speed indicator includes: a shape representative of a range of longitudinal translation speeds; and a marker positioned within the shape and representative of the determined longitudinal translation speed. The system where the speed indicator includes: a region of the shape identifying an ideal range for the longitudinal translation speed, where the region extends from a first portion representative of a minimum ideal translation speed to an opposite, second portion representative of a maximum ideal translation speed. The system where the processor circuit is configured to: determine at least one of: a length estimate of the body lumen based on the longitudinal translation speed; or a volume estimate of the body lumen based on the longitudinal translation speed and an area of the body lumen in the plurality of intraluminal ultrasound images; and output at least one of the length estimate or the volume estimate via the screen display. The system where the screen display further includes a stylized diagram of the body lumen. The system where the screen display further includes a position of the intraluminal ultrasound imaging catheter within the stylized diagram. The system where the screen display further includes a trail indicating past positions of the intraluminal ultrasound imaging catheter. The system where the trail is color coded in the screen display to indicate past longitudinal translation speeds of the intraluminal ultrasound imaging catheter. The system further including: the intraluminal ultrasound imaging catheter. Implementations of the described techniques may include hardware, a method or process, or computer software on a computer-accessible medium.

One general aspect includes an intraluminal ultrasound imaging method, including: receiving, at a processor circuit in communication with an intraluminal ultrasound imaging catheter, a plurality of intraluminal ultrasound images obtained by the intraluminal ultrasound imaging catheter while the intraluminal ultrasound imaging catheter is moved through a body lumen of a patient; determining, with the processor circuit, a longitudinal translation speed of the intraluminal ultrasound imaging catheter based on the plurality of intraluminal ultrasound images and a known time interval between each of plurality of intraluminal ultrasound images; and outputting, to a display in communication with the processor circuit, a screen display including a speed indicator based on the longitudinal translation speed. Other embodiments of this aspect include corresponding computer systems, apparatus, and computer programs recorded on one or more computer storage devices, each configured to perform the actions of the methods.

One general aspect includes an intravascular ultrasound imaging system for use in peripheral vasculature, the system including: an intravascular ultrasound imaging catheter configured to obtain a plurality of intravascular ultrasound images while the intravascular ultrasound imaging catheter is moved through a peripheral blood vessel of a patient; a processor circuit configured for communication with the intravascular ultrasound imaging catheter, where the processor circuit is configured to: receive the plurality of intravascular ultrasound images obtained by the intravascular ultrasound imaging catheter; determine a longitudinal translation speed of the intravascular ultrasound imaging catheter through the peripheral blood vessel based on the plurality of intravascular ultrasound images and a known time interval between each of plurality of intravascular ultrasound images; and output, to a display in communication with the processor circuit, a screen display including a speed indicator based on the longitudinal translation speed. Other embodiments of this aspect include corresponding computer systems, apparatus, and computer programs recorded on one or more computer storage devices, each configured to perform the actions of the methods.

This Summary is provided to introduce a selection of concepts in a simplified form that are further described below in the Detailed Description. This Summary is not intended to identify key features or essential features of the claimed subject matter, nor is it intended to limit the scope of the claimed subject matter. A more extensive presentation of features, details, utilities, and advantages of the pullback speed management system, as defined in the claims, is provided in the following written description of various embodiments of the disclosure and illustrated in the accompanying drawings.

BRIEF DESCRIPTION OF THE DRAWINGS

Illustrative embodiments of the present disclosure will be described with reference to the accompanying drawings, of which:

FIG. 20b illustrates a tomographic intraluminal image of a vessel with a vessel wall that is farther along the pullback than the image in FIG. 20a.

FIG. 21b illustrates a tomographic intraluminal image of a vessel with a vessel wall that is farther along the pullback than the image in FIG. 20a.

DETAILED DESCRIPTION

Figure 1:
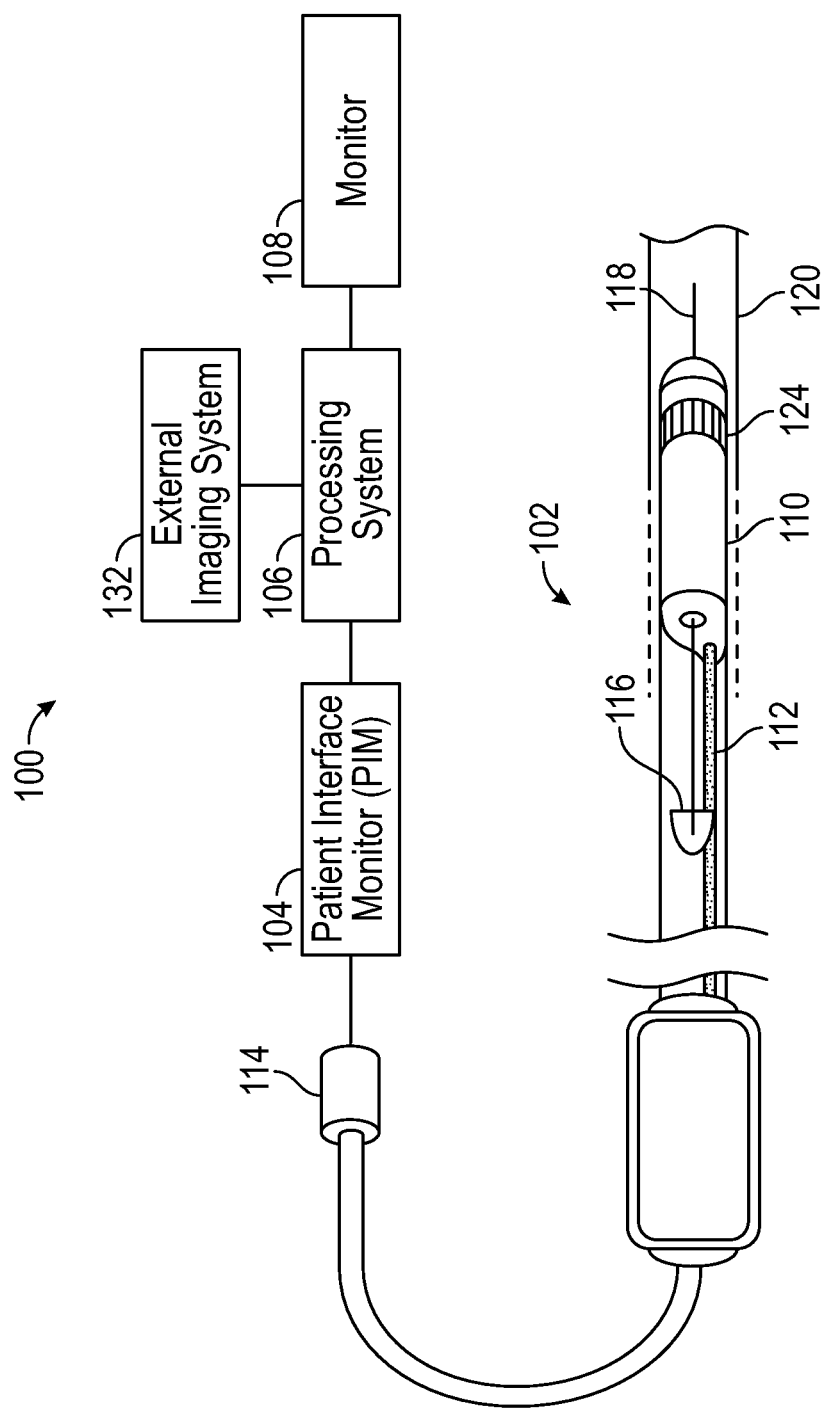
FIG. 1 is a diagrammatic schematic view of an intraluminal imaging system, according to aspects of the present disclosure.

The present disclosure relates generally to medical imaging, including imaging associated with a body lumen of a patient using an intraluminal imaging device. For example, the present disclosure describes systems, devices, and methods for determining the movement speed of an intravascular probe during an IVUS pullback procedure or other intravascular procedure. In accordance with at least one embodiment of the present disclosure, a system is provided for determining the pullback speed based on the IVUS images themselves, and displaying the speed as navigation information to a clinician with respect to a desired range of speeds. This may be particularly useful during manually controlled intravascular procedures where a consistent probe speed (e.g., pullback speed) within a target range is desired. Determining pullback speed using the IVUS images themselves is different than determining speed by tracking the position of the catheter in extraluminal images (e.g., fluoroscopic images), and in many cases requires fewer steps and less equipment. This system is hereinafter referred to as a pullback speed management system.

The devices, systems, and methods described herein can include one or more features described in U.S. Provisional App. No. 62/750,983, filed 26 Oct. 2018, U.S. Provisional App. No. 62/751,268, filed 26 Oct. 2018, U.S. Provisional App. No. 62/751,289, filed 26 Oct. 2018, U.S. Provisional App. No. 62/750,996, filed 26 Oct. 2018, U.S. Provisional App. No. 62/751,167, filed 26 Oct. 2018, and U.S. Provisional App. No. 62/751,185, filed 26 Oct. 2018, each of which is hereby incorporated by reference in its entirety as though fully set forth herein.

The devices, systems, and methods described herein can also include one or more features described in U.S. Provisional App. No. U.S. Ser. No. 62/642,847, filed Mar. 14, 2018 (and a Non-Provisional Application filed therefrom on Mar. 12, 2019 as U.S. Ser. No. 16/351,175), U.S. Provisional App. No. 62/712,009, filed Jul. 30, 2018, U.S. Provisional App. No. 62/711,927, filed Jul. 30, 2018, and U.S. Provisional App. No. 62/643,366, filed Mar. 15, 2018 (and a Non-Provisional Application filed therefrom on Mar. 15, 2019 as U.S. Ser. No. 16/354,970), each of which is hereby incorporated by reference in its entirety as though fully set forth herein.

The devices, systems, and methods described herein can also include one or more features described in U.S. Provisional App. No. 62/725,867, filed Aug. 31, 2018, and titled "Intravascular Device Movement Speed Guidance and associated Devices, Systems, and Methods," and U.S. Ser. No. 16/542,001, filed Aug. 15, 2019, which are hereby incorporated by reference in their entirety as though fully set forth herein.

The present disclosure substantially aids a clinician in sensing, controlling, and maintaining the speed at which an intravascular imaging probe or intraluminal imaging probe is pushed or pulled within a vessel or lumen of a patient, by providing visual, symbolic, alphanumeric, and sensory information about the probe's movement speed during intraluminal medical imaging procedures. The speed information may include gauges, dials, bar indicators, numerical and symbolic displays. Implemented on a medical imaging console (e.g., an intraluminal imaging console) in communication with a medical imaging sensor (e.g., an intraluminal ultrasound sensor), the pullback speed management system disclosed herein provides both time savings and an improvement in the quality and consistency of captured images. This improved imaging workflow transforms an irregular and inconsistent imaging process into a more controlled and repeatable process. This occurs for example without the normally routine need for clinicians to train for consistent pullback within a narrow range of acceptable pullback speeds. This unconventional approach improves the functioning of the medical imaging console and sensor, by permitting more consistent images to be captured from existing systems that lack hardware-based speed controls.

The pullback speed management system may be implemented as a set of logical branches and mathematical operations, whose outputs are viewable on a display, and operated by a control process executing on a processor that accepts user inputs from a keyboard, mouse, or touchscreen interface, and that is in communication with one or more medical imaging sensors (e.g., intraluminal ultrasound sensors). In that regard, the control process performs certain specific operations in response to different inputs or selections made by a user at the start of an imaging procedure, and may also respond to inputs made by the user during the procedure. Certain structures, functions, and operations of the processor, display, sensors, and user input systems are known in the art, while others are recited herein to enable novel features or aspects of the present disclosure with particularity.

Various types of intraluminal imaging systems are used in diagnosing and treating diseases. For example, intravascular ultrasound (IVUS) imaging is used as a diagnostic tool for visualizing vessels within a body of a patient. This may aid in assessing diseased or compressed vessels, such as arteries or veins, within the human body to determine the need for treatment, to optimize treatment, and/or to assess a treatment's effectiveness (e.g., through imaging of the vessel before and after treatment).

In some cases, intraluminal imaging is carried out with an IVUS device including one or more ultrasound transducers. The IVUS device may be passed into the vessel and guided to the area to be imaged. The transducers emit ultrasonic energy and receive ultrasound echoes reflected from the vessel. The ultrasound echoes are processed to create an image of the vessel of interest. The image of the vessel of interest may include one or more lesions or blockages in the vessel. A stent may be placed within the vessel to treat these blockages and intraluminal imaging may be carried out to view the placement of the stent within the vessel. Other types of treatment include thrombectomy, ablation, angioplasty, pharmaceuticals, etc.

In some embodiments, the pullback speed management system includes screen displays that provide a clinician with guidance during an IVUS pullback in peripheral vasculature, or other intravascular imaging procedure. The screen displays provide real-time feedback of the speed of the catheter or imaging probe within the vessel, both in absolute terms and with respect to the minimum and maximum desired speeds for optimal image acquisition.

Being able to control speed is critical to obtain appropriate ultrasound image quality, so that the user is able to interpret the image to conform diagnosis (e.g., a lesion's length and severity) and to confirm treatment choice (e.g., balloon and stent diameter and length). Control of pullback speed is also essential to ensure proper functioning of image recognition and image interpretation algorithms. Excessive pullback speed may result in some portions of the anatomy being skipped over during the imaging process, such that they do not appear in the image set at all, thus making the dataset difficult to interpret.

Currently, for peripheral catheters, length is estimated by physicians by looking at the fluoroscopy image and considering markers on IVUS image sequence, or by counting on their own experience in interpreting position of body landmarks or other anatomical features. Keeping a steady pullback velocity would enable more accurate length estimation, which is important for example to determine stent and balloon deployment areas. Thus, the system may measure a speed, rate, or velocity, either in absolute terms or relative to a desired or reference speed, rate, or velocity, or ranged thereof. Moreover, estimating length could also lead to automatic vessel volume measurements (area times length), deriving from automatic luminal area measurements and length (e.g., measured speed multiplied by elapsed time, or the integral of speed over time). In fact, measuring pre-treatment volume and post-treatment volume may provide physicians with an absolute measurement of material (and clot) removed from the vessel during the treatment, thus possibly becoming a quantitative indicator for treatment success.

To guide physicians in reaching and maintaining a constant speed (e.g., while performing a pullback), a 'speed indicator' is included on the IVUS screen, as described in the images below. This speed indicator shows the IVUS operator the catheter's actual speed (i.e., longitudinal translation velocity) within the vessel, and is activated automatically during the 'Record' phase of a procedure. In some embodiments, the system reports to the operator not only the speed itself, but also whether the speed is within the proper range to ensure adequate pullback recording. The system then suggests the right speed range by a number of different visible cues. For example, a too fast/slow velocity can be suggested by color coding (see for example FIGS. 8 and 9). This may involve a numerical measurement and reporting of the velocity, or a variety of different ways to communicate to the user the correct range of speed to reach and keep during pullback (see for example FIGS. 12, 13, and 16).

Thanks to this constant velocity, a rough estimation of pullback length can be derived, this being extremely valuable for physicians to decide upon stent length right after pullback and measurement review, or to possibly derive vessel volume (from automatic area measurement and length estimation) pre-post treatment as indication for treatment success.

This disclosure applies for example to Philips Volcano's peripheral catheters IVUS PV 0.014, PV 0.018, PV0.035, Pioneer Plus IVUS-guided re-entry catheter, and other products being used in the peripheral area where speed control could be used and benefit the treatment delivery. These may include, but are not limited to, thrombectomy devices (see Genesis—in AD within IGT) and Atherectomy devices (e.g., Phoenix Turbo power laser atherectomy), when used in combination with IVUS.

These descriptions are provided for exemplary purposes only, and should not be considered to limit the scope of the pullback speed management system. Certain features may be added, removed, or modified without departing from the spirit of the claimed subject matter.

For the purposes of promoting an understanding of the principles of the present disclosure, reference will now be made to the embodiments illustrated in the drawings, and specific language will be used to describe the same. It is nevertheless understood that no limitation to the scope of the disclosure is intended. Any alterations and further modifications to the described devices, systems, and methods, and any further application of the principles of the present disclosure are fully contemplated and included within the present disclosure as would normally occur to one skilled in the art to which the disclosure relates. In particular, it is fully contemplated that the features, components, and/or steps described with respect to one embodiment may be combined with the features, components, and/or steps described with respect to other embodiments of the present disclosure. For the sake of brevity, however, the numerous iterations of these combinations will not be described separately.

FIG. 1 is a diagrammatic schematic view of an intraluminal imaging system incorporating the pullback speed management system, according to aspects of the present disclosure. The intraluminal imaging system 100 can be an intravascular ultrasound (IVUS) imaging system in some embodiments. The intraluminal imaging system 100 may include an intraluminal device 102, a patient interface module (PIM) 104, a console or processing system 106, a monitor 108, and an external imaging system 132 which may include angiography, ultrasound, X-ray, computed tomography (CT), magnetic resonance imaging (MRI), or other imaging technologies, equipment, and methods. The intraluminal device 102 is sized and shaped, and/or otherwise structurally arranged to be positioned within a body lumen of a patient. For example, the intraluminal device 102 can be a catheter, guide wire, guide catheter, pressure wire, and/or flow wire in various embodiments. In some circumstances, the system 100 may include additional elements and/or may be implemented without one or more of the elements illustrated in FIG. 1. For example, the system 100 may omit the external imaging system 132.

The intraluminal imaging system 100 (or intravascular imaging system) can be any type of imaging system suitable for use in the lumens or vasculature of a patient. In some embodiments, the intraluminal imaging system 100 is an intraluminal ultrasound (IVUS) imaging system. In other embodiments, the intraluminal imaging system 100 may include systems configured for forward looking intraluminal ultrasound (FL-IVUS) imaging, intraluminal photoacoustic (IVPA) imaging, intracardiac echocardiography (ICE), transesophageal echocardiography (TEE), and/or other suitable imaging modalities.

It is understood that the system 100 and/or device 102 can be configured to obtain any suitable intraluminal imaging data. In some embodiments, the device 102 may include an imaging component of any suitable imaging modality, such as optical imaging, optical coherence tomography (OCT), etc. In some embodiments, the device 102 may include any suitable non-imaging component, including a pressure sensor, a flow sensor, a temperature sensor, an optical fiber, a reflector, a mirror, a prism, an ablation element, a radio frequency (RF) electrode, a conductor, or combinations thereof. Generally, the device 102 can include an imaging element to obtain intraluminal imaging data associated with the lumen 120. The device 102 may be sized and shaped (and/or configured) for insertion into a vessel or lumen 120 of the patient.

The system 100 may be deployed in a catheterization laboratory having a control room. The processing system 106 may be located in the control room. Optionally, the processing system 106 may be located elsewhere, such as in the catheterization laboratory itself. The catheterization laboratory may include a sterile field while its associated control room may or may not be sterile depending on the procedure to be performed and/or on the health care facility. The catheterization laboratory and control room may be used to perform any number of medical imaging procedures such as angiography, fluoroscopy, CT, IVUS, virtual histology (VH), forward looking IVUS (FL-IVUS), intraluminal photoacoustic (IVPA) imaging, a fractional flow reserve (FFR) determination, a coronary flow reserve (CFR) determination, optical coherence tomography (OCT), computed tomography, intracardiac echocardiography (ICE), forward-looking ICE (FLICE), intraluminal palpography, transesophageal ultrasound, fluoroscopy, and other medical imaging modalities, or combinations thereof. In some embodiments, device 102 may be controlled from a remote location such as the control room, such than an operator is not required to be in close proximity to the patient.

The intraluminal device 102, PIM 104, monitor 108, and external imaging system 132 may be communicatively coupled directly or indirectly to the processing system 106. These elements may be communicatively coupled to the medical processing system 106 via a wired connection such as a standard copper link or a fiber optic link and/or via wireless connections using IEEE 802.11 Wi-Fi standards, Ultra Wide-Band (UWB) standards, wireless FireWire, wireless USB, or another high-speed wireless networking standard. The processing system 106 may be communicatively coupled to one or more data networks, e.g., a TCP/IP-based local area network (LAN). In other embodiments, different protocols may be utilized such as Synchronous Optical Networking (SONET). In some cases, the processing system 106 may be communicatively coupled to a wide area network (WAN). The processing system 106 may utilize network connectivity to access various resources. For example, the processing system 106 may communicate with a Digital Imaging and Communications in Medicine (DICOM) system, a Picture Archiving and Communication System (PACS), and/or a Hospital Information System via a network connection.

At a high level, an ultrasound imaging intraluminal device 102 emits ultrasonic energy from a transducer array 124 included in scanner assembly 110 mounted near a distal end of the intraluminal device 102. The ultrasonic energy is reflected by tissue structures in the medium (such as a lumen 120) surrounding the scanner assembly 110, and the ultrasound echo signals are received by the transducer array 124. The scanner assembly 110 generates electrical signal(s) representative of the ultrasound echoes. The scanner assembly 110 can include one or more single ultrasound transducers and/or a transducer array 124 in any suitable configuration, such as a planar array, a curved array, a circumferential array, an annular array, etc. For example, the scanner assembly 110 can be a one-dimensional array or a two-dimensional array in some instances. In some instances, the scanner assembly 110 can be a rotational ultrasound device. The active area of the scanner assembly 110 can include one or more transducer materials and/or one or more segments of ultrasound elements (e.g., one or more rows, one or more columns, and/or one or more orientations) that can be uniformly or independently controlled and activated. The active area of the scanner assembly 110 can be patterned or structured in various basic or complex geometries. The scanner assembly 110 can be disposed in a side-looking orientation (e.g., ultrasonic energy emitted perpendicular and/or orthogonal to the longitudinal axis of the intraluminal device 102) and/or a forward-looking looking orientation (e.g., ultrasonic energy emitted parallel to and/or along the longitudinal axis). In some instances, the scanner assembly 110 is structurally arranged to emit and/or receive ultrasonic energy at an oblique angle relative to the longitudinal axis, in a proximal or distal direction. In some embodiments, ultrasonic energy emission can be electronically steered by selective triggering of one or more transducer elements of the scanner assembly 110.

The ultrasound transducer(s) of the scanner assembly 110 can be a piezoelectric micromachined ultrasound transducer (PMUT), capacitive micromachined ultrasonic transducer (CMUT), single crystal, lead zirconate titanate (PZT), PZT composite, other suitable transducer type, and/or combinations thereof. In an embodiment the ultrasound transducer array 124 can include any suitable number of individual transducer elements or acoustic elements between 1 acoustic element and 1000 acoustic elements, including values such as 2 acoustic elements, 4 acoustic elements, 36 acoustic elements, 64 acoustic elements, 128 acoustic elements, 500 acoustic elements, 812 acoustic elements, and/or other values both larger and smaller.

The PIM 104 transfers the received echo signals to the processing system 106 where the ultrasound image (including the flow information) is reconstructed and displayed on the monitor 108. The console or processing system 106 can include a processor and a memory. The processing system 106 may be operable to facilitate the features of the intraluminal imaging system 100 described herein. For example, the processor can execute computer readable instructions stored on the non-transitory tangible computer readable medium.

The PIM 104 facilitates communication of signals between the processing system 106 and the scanner assembly 110 included in the intraluminal device 102. This communication may include providing commands to integrated circuit controller chip(s) within the intraluminal device 102, selecting particular element(s) on the transducer array 124 to be used for transmit and receive, providing the transmit trigger signals to the integrated circuit controller chip(s) to activate the transmitter circuitry to generate an electrical pulse to excite the selected transducer array element(s), and/or accepting amplified echo signals received from the selected transducer array element(s) via amplifiers included on the integrated circuit controller chip(s). In some embodiments, the PIM 104 performs preliminary processing of the echo data prior to relaying the data to the processing system 106. In examples of such embodiments, the PIM 104 performs amplification, filtering, and/or aggregating of the data. In an embodiment, the PIM 104 also supplies high- and low-voltage DC power to support operation of the intraluminal device 102 including circuitry within the scanner assembly 110.

The processing system 106 receives echo data from the scanner assembly 110 by way of the PIM 104 and processes the data to reconstruct an image of the tissue structures in the medium surrounding the scanner assembly 110. Generally, the device 102 can be utilized within any suitable anatomy and/or body lumen of the patient. The processing system 106 outputs image data such that an image of the vessel or lumen 120, such as a cross-sectional IVUS image of the lumen 120, is displayed on the monitor 108. Lumen 120 may represent fluid filled or fluid-surrounded structures, both natural and man-made. Lumen 120 may be within a body of a patient. Lumen 120 may be a blood vessel, such as an artery or a vein of a patient's vascular system, including cardiac vasculature, peripheral vasculature, neural vasculature, renal vasculature, and/or or any other suitable lumen inside the body. For example, the device 102 may be used to examine any number of anatomical locations and tissue types, including without limitation, organs including the liver, heart, kidneys, gall bladder, pancreas, lungs; ducts; intestines; nervous system structures including the brain, dural sac, spinal cord and peripheral nerves; the urinary tract; as well as valves within the blood, chambers or other parts of the heart, and/or other systems of the body. In addition to natural structures, the device 102 may be used to examine man-made structures such as, but without limitation, heart valves, stents, shunts, filters and other devices.

The controller or processing system 106 may include a processing circuit having one or more processors in communication with memory and/or other suitable tangible computer readable storage media. The controller or processing system 106 may be configured to carry out one or more aspects of the present disclosure. In some embodiments, the processing system 106 and the monitor 108 are separate components. In other embodiments, the processing system 106 and the monitor 108 are integrated in a single component. For example, the system 100 can include a touch screen device, including a housing having a touch screen display and a processor. The system 100 can include any suitable input device, such as a touch sensitive pad or touch screen display, keyboard/mouse, joystick, button, etc., for a user to select options shown on the monitor 108. The processing system 106, the monitor 108, the input device, and/or combinations thereof can be referenced as a controller of the system 100. The controller can be in communication with the device 102, the PIM 104, the processing system 106, the monitor 108, the input device, and/or other components of the system 100.

In some embodiments, the intraluminal device 102 includes some features similar to traditional solid-state IVUS catheters, such as the EagleEye® catheter available from Volcano Corporation and those disclosed in U.S. Pat. No. 7,846,101 hereby incorporated by reference in its entirety. For example, the intraluminal device 102 may include the scanner assembly 110 near a distal end of the intraluminal device 102 and a transmission line bundle 112 extending along the longitudinal body of the intraluminal device 102. The cable or transmission line bundle 112 can include a plurality of conductors, including one, two, three, four, five, six, seven, or more conductors.

The transmission line bundle 112 terminates in a PIM connector 114 at a proximal end of the intraluminal device 102. The PIM connector 114 electrically couples the transmission line bundle 112 to the PIM 104 and physically couples the intraluminal device 102 to the PIM 104. In an embodiment, the intraluminal device 102 further includes a guidewire exit port 116. Accordingly, in some instances the intraluminal device 102 is a rapid-exchange catheter. The guidewire exit port 116 allows a guidewire 118 to be inserted towards the distal end in order to direct the intraluminal device 102 through the lumen 120.

The monitor 108 may be a display device such as a computer monitor or other type of screen. The monitor 108 may be used to display selectable prompts, instructions, and visualizations of imaging data to a user. In some embodiments, the monitor 108 may be used to provide a procedure-specific workflow to a user to complete an intraluminal imaging procedure. This workflow may include performing a pre-stent plan to determine the state of a lumen and potential for a stent, as well as a post-stent inspection to determine the status of a stent that has been positioned in a lumen. The workflow may be presented to a user as any of the displays or visualizations shown in FIGS. 5-7.

The external imaging system 132 can be configured to obtain x-ray, radiographic, angiographic/venographic (e.g., with contrast), and/or fluoroscopic (e.g., without contrast) images of the body of patient (including the vessel 120). External imaging system 132 may also be configured to obtain computed tomography images of the body of patient (including the vessel 120). The external imaging system 132 may include an external ultrasound probe configured to obtain ultrasound images of the body of the patient (including the vessel 120) while positioned outside the body. In some embodiments, the system 100 includes other imaging modality systems (e.g., MRI) to obtain images of the body of the patient (including the vessel 120). The processing system 106 can utilize the images of the body of the patient in conjunction with the intraluminal images obtained by the intraluminal device 102.

Figure 2:
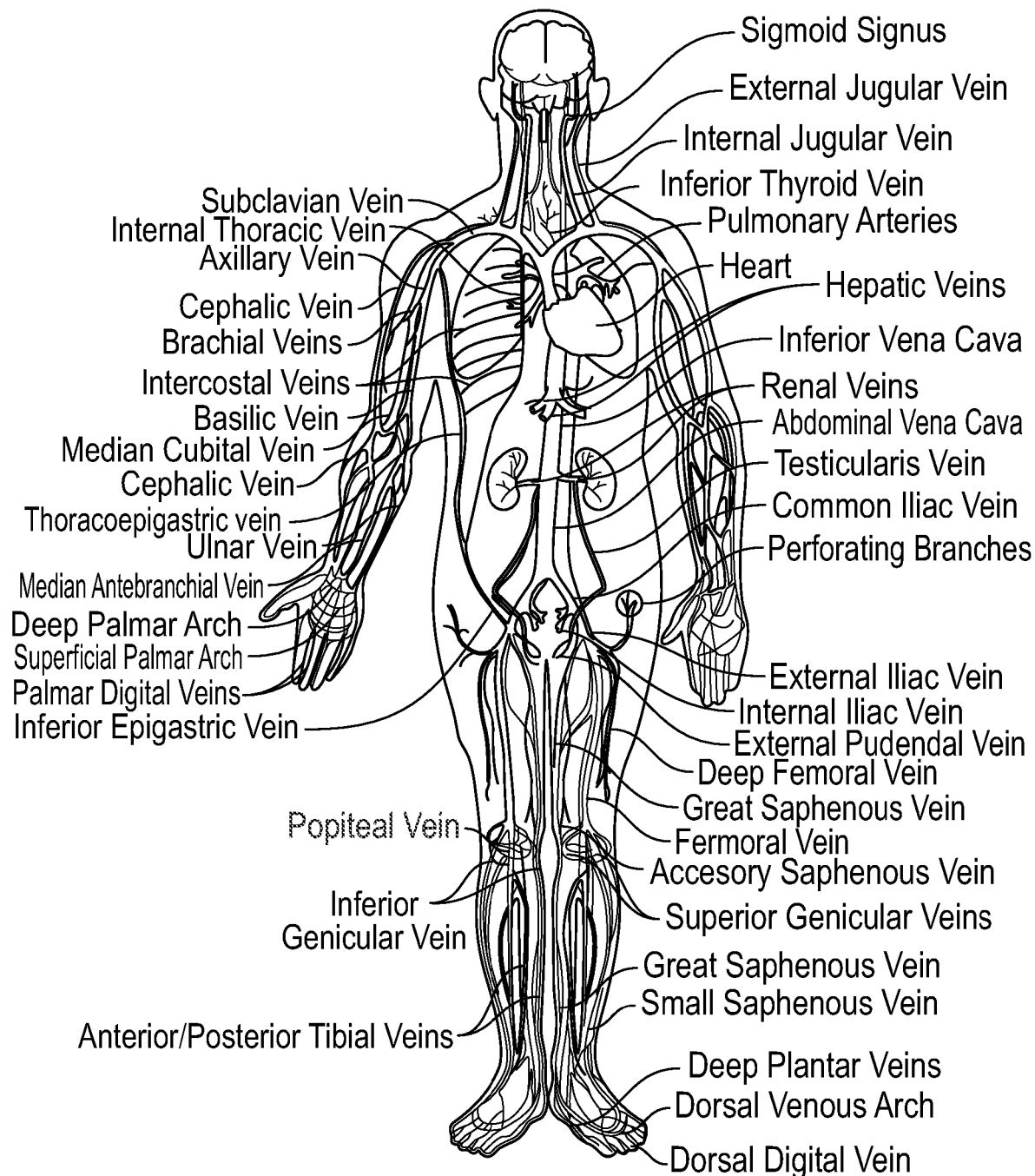
FIG. 2 illustrates blood vessels (e.g., arteries and veins) in the human body.

FIG. 2 illustrates blood vessels (e.g., arteries and veins) in the human body. For example, veins of the human body are labeled. Aspects of the present disclosure can be related to peripheral vasculature, e.g., veins in the torso or legs.

Occlusions can occur in arteries or veins. An occlusion can be generally representative of any blockage or other structural arrangement that results in a restriction to the flow of fluid through the lumen (e.g., an artery or a vein), for example, in a manner that is deleterious to the health of the patient. For example, the occlusion narrows the lumen such that the cross-sectional area of the lumen and/or the available space for fluid to flow through the lumen is decreased. Where the anatomy is a blood vessel, the occlusion may be a result of narrowing due to compression (e.g., from external vessels), plaque buildup, including without limitation plaque components such as fibrous, fibro-lipidic (fibro fatty), necrotic core, calcified (dense calcium), blood, and/or different stages of thrombus (acute, sub-acute, chronic, etc.). In some instances, the occlusion can be referenced as thrombus, a stenosis, and/or a lesion. Generally, the composition of the occlusion will depend on the type of anatomy being evaluated. Healthier portions of the anatomy may have a uniform or symmetrical profile (e.g., a cylindrical profile with a circular cross-sectional profile). The occlusion may not have a uniform or symmetrical profile. Accordingly, diseased or compressed portions of the anatomy, with the occlusion, will have a non-symmetric and/or otherwise irregular profile. The anatomy can have one occlusion or multiple occlusions.

Build-up of occlusion (e.g., thrombus, deep vein thrombosis or DVT, chronic total occlusion or CTO, etc.) is one way in which the cross-sectional area of the vein in the peripheral vasculature (e.g., torso, abdomen, groin, leg) may be reduced. Other anatomy that contacts the vein can also reduce its cross-sectional area, thereby restricting blood flow therethrough. For example, arteries or ligaments in the torso, abdomen, groin, or leg can press against a vein, which changes the shape of the vein and reduces its cross-sectional area. Such reductions in cross-sectional area resulting from contact with other anatomy can be referenced as compression, in that the walls of the vein are compressed as a result of the contact with the artery or ligament.

Figure 3:
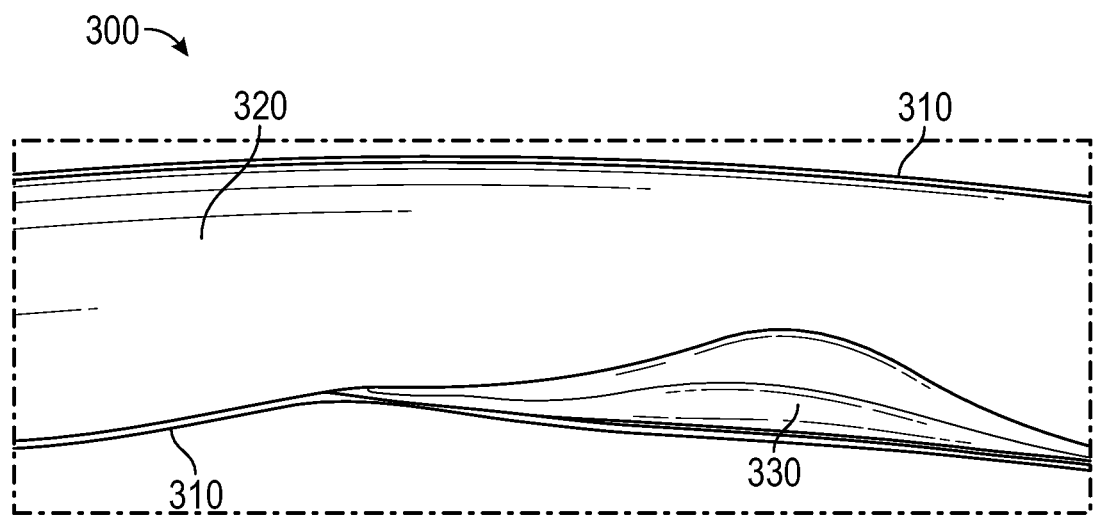
FIG. 3 illustrates a blood vessel incorporating a compression.

FIG. 3 illustrates a blood vessel 300 incorporating a compression 330. The compression 330 occurs outside the vessel walls 310 and may restrict the flow of blood 320. The compression may be caused by other anatomical structures outside the blood vessel 300, including but not limited to a tendon, ligament, or neighboring lumen.

Figure 4:
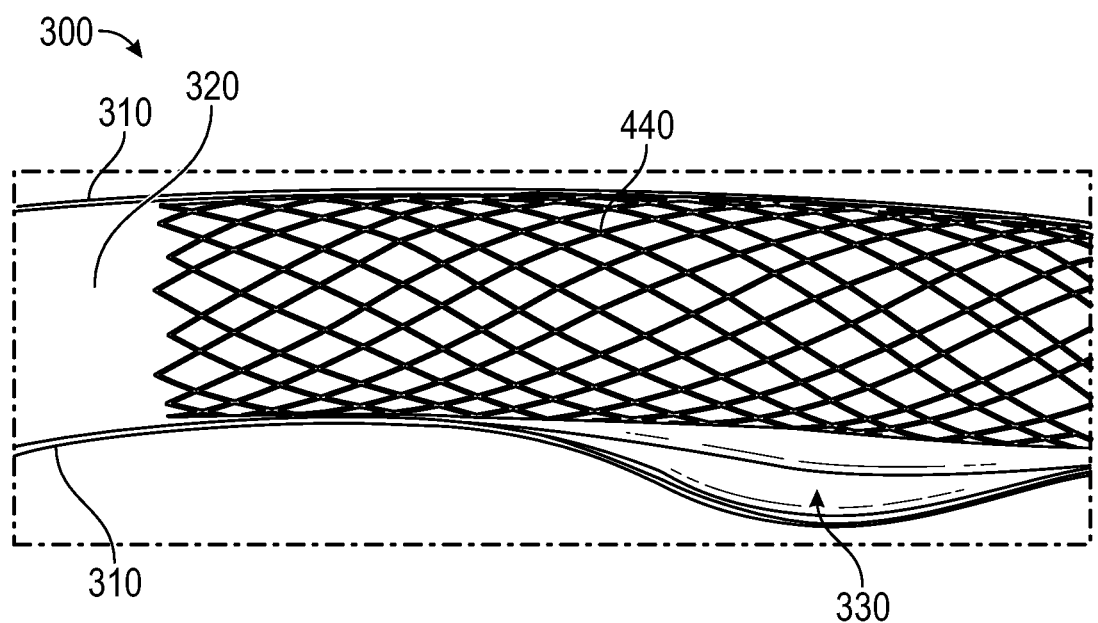
FIG. 4 illustrates a blood vessel incorporating a compression and with a stent expanded inside it to restore flow.

FIG. 4 illustrates a blood vessel 300 incorporating a compression 330 and with a stent 440 expanded inside it to restore flow. The stent 440 displaces and arrests the compression 330, pushing the vessel walls 310 outward, thus reducing the flow restriction for the blood 320. Other treatment options for alleviating an occlusion may include but are not limited to thrombectomy, ablation, angioplasty, and pharmaceuticals. However, in a large majority of cases it may be highly desirable to obtain accurate and timely intravascular images of the affected area, along with accurate and detailed knowledge of the location, orientation, length, and volume of the affected area prior to, during, or after treatment.

FIGS. 5-9 and 10-21 (was 3-19) illustrate exemplary screen displays or graphical user interfaces (GUIs). The screen displays can be shown on a display of the system 100, for example, a display of a console, a cart, a bedside controller, a mobile device (e.g., smartphone, tablet, personal digital assistant or PDA), a laptop computer, a desktop computer, etc. The display can be touchscreen display. The display can be in communication with a computer with a processing circuit (e.g., one or more processors and memory). The processing circuit can generate and output the display data to cause the display to show the screen displays of FIGS. 5-9 and 10-21. The computer, processing circuit, and/or processor can also be in communication with a user interface on which user provides inputs. The inputs can be selections of items on the screen displays. The user interface can be a touchscreen display in some instances. The user interface can be a keyboard, a mouse, a controller with buttons, joystick, etc.

FIGS. 5-9 illustrate screen displays providing the user guidance during a IVUS pullback in peripheral vasculature. The screen displays may highlight the segments of the vasculature, label and color code the segments, and automatically provide reference and compression measures (e.g., cross-sectional lumen area, diameter, etc.) within each of the segments. Additionally, the screen displays provide real time feedback for the user about pullback speed, since consistent pullback speed within a desired speed range is necessary for generation of clear intravascular images (e.g., IVUS images). The GUIs can also provide for image quality improvement by provided the ability to adjust contrast, gain, focus, and/or other image settings. Image quality can also be improved based on providing feedback to the user to reach the correct pullback speed to obtain sufficient amount of high quality IVUS data.

As shown, the screen displays of FIGS. 5-9 include a graphical representation of the peripheral vasculature (e.g., inferior vena cava, abdominal vena cava, renal veins, left and right common iliac veins, left and right common femoral veins, etc.) in which the intraluminal ultrasound device (e.g., IVUS catheter) is positioned. The graphical representations can be an illustration or cartoon of the vasculature and/or an x-ray/CT/MRI image. For example, the graphical representation can be a roadmap image. The graphical representations can be formed from the obtained IVUS images. The graphical representations illustrate the longitudinal extent of the vasculature and can be referenced as a longitudinal display or image longitudinal display (ILD).

Figure 5:
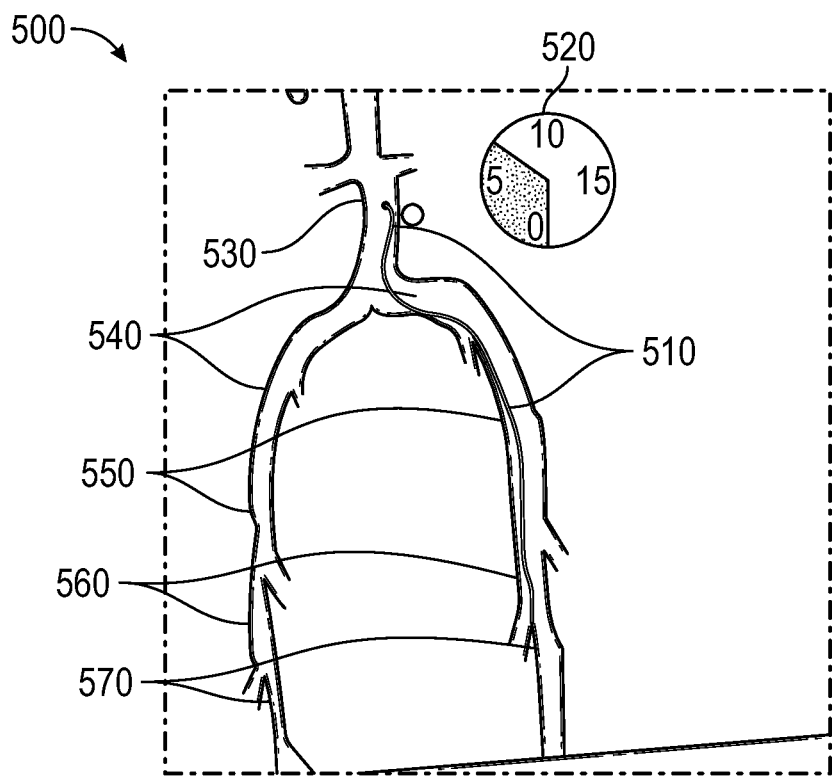
FIG. 5 shows a screen display of an exemplary cartoon roadmap or virtual venogram at the start of a pullback procedure of an imaging catheter in the inferior vena cava or abdominal vena cava in accordance with at least one embodiment of the present disclosure.

A graphical representation of the IVUS catheter, including the flexible elongate member positioned within the vasculature and the transducer array at the distal portion of the flexible elongate member, is also displayed. The position of the IVUS catheter within the vasculature changes from FIGS. 5-9 during the imaging pullback. As shown in FIG. 5, the IVUS catheter starts with transducer array positioned within the inferior or abdominal vena cava. During the pullback, the transducer array moves longitudinally within the vasculature, through the right iliac vein (e.g., FIG. 7), to the right femoral vein (e.g., FIG. 9). Position of the transducer may be determined for example through co-registration of IVUS images with external images (e.g., fluoroscopic images), or may be estimated based on user input identifying which segment of vasculature the transducer is in.

FIG. 5 shows a screen display of an exemplary cartoon roadmap or virtual venogram 500 at the start of a pullback procedure of an imaging catheter 510 in the inferior vena cava or abdominal vena cava 530 in accordance with at least one embodiment of the present disclosure. A speed indicator 520 is provided to provide navigation information and guidance about the pullback speed. The pullback speed affects the amount of imaging data collected at locations along the length of the vasculature, and therefore the image quality of the IVUS images at those locations. Different colors, shadings, text, numerical values, etc. within the speed indicator 520 can alert the user about whether to speed up (go faster), slow down (go slower), and/or maintain speed during the pullback. For example, a speed gauge with numerical values is shown in FIGS. 5-9. All or a portion of the speed gauge can be colored to guide the user. For example, in FIGS. 5, 6, and 7, a green highlight on the speed gauge indicates that the user is pullback speed is appropriate and should be maintained.

Also visible are the left and right common iliac vein (CIV) 540 left and right external iliac vein (EIV) 550, left and right common femoral veins (CFV) 560, and left and right femoral veins (F) 570.

Figure 6:
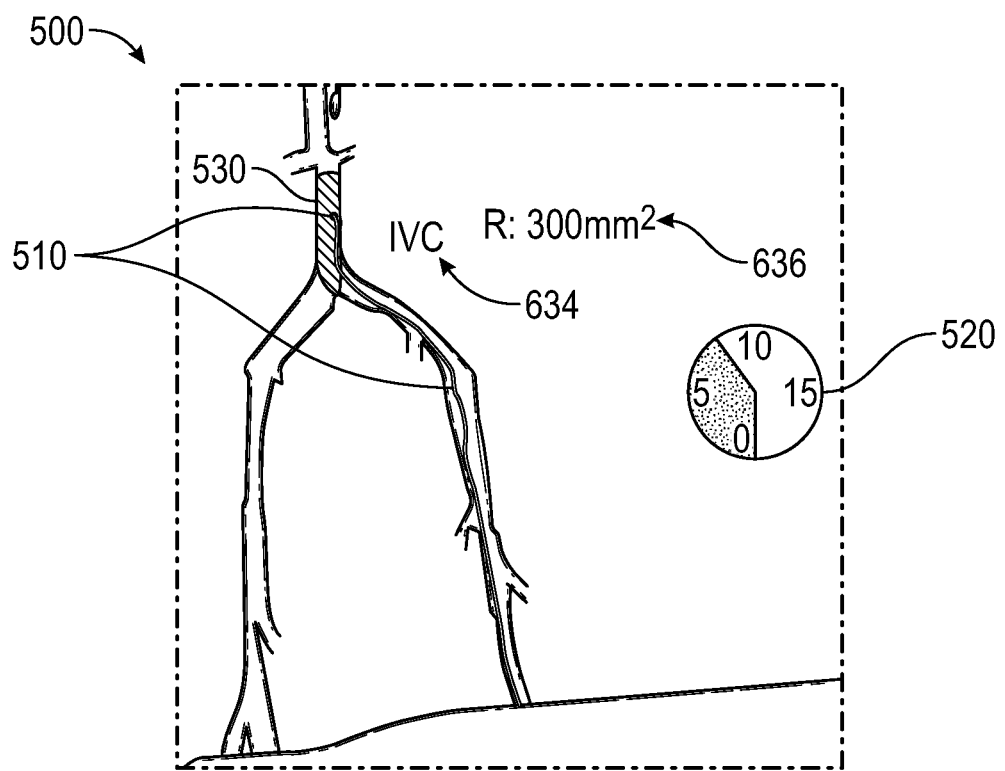
FIG. 6 shows a screen display of an exemplary cartoon roadmap or virtual venogram during a pullback procedure of an imaging catheter in the inferior vena cava, in accordance with at least one embodiment of the present disclosure.

FIG. 6 shows a screen display of an exemplary cartoon roadmap or virtual venogram 500 during a pullback procedure of an imaging catheter 510 in the inferior vena cava, in accordance with at least one embodiment of the present disclosure. In this example, the virtual venogram 500 now includes a text label 634 ("IVC") adjacent to the vasculature to identify the inferior vena cava 530 as the segment of the vasculature currently occupied by the catheter 510, corresponding to the highlighted segment of the virtual venogram 500. For example, the label can be an abbreviation or the full form of the name of the corresponding vasculature segment.

The screen display also automatically provides a statistically representative reference value 636 associated with the vasculature segment 530, adjacent to the vasculature segment 530. The reference value may be an expected value for a healthy vessel, based on literature, for example. The reference value may be the value for a healthy vessel for the particular patient. For example, the reference value may be a numerical value of the cross-sectional lumen area. The numerical value shown in FIG. 6 is exemplary only and does not necessarily reflect the values associated with the specific anatomy. In this example, the inferior vena cava or abdominal vena cava 530 has been colored, shaded, and/or highlighted in the virtual venogram 500, such as in a first color (e.g., blue). The color for the IVC segment can be different than colors associated with other vasculature segments to indicate that it is the start of the pullback. The color of the segment can also indicate that no compression measure is determined from the obtained IVUS data or that the compression measure is equal or approximately equal to the reference measure.

In this example, the speed indicator 520 may be colored green, to indicate that the pullback speed is within the desired range.

Figure 7:
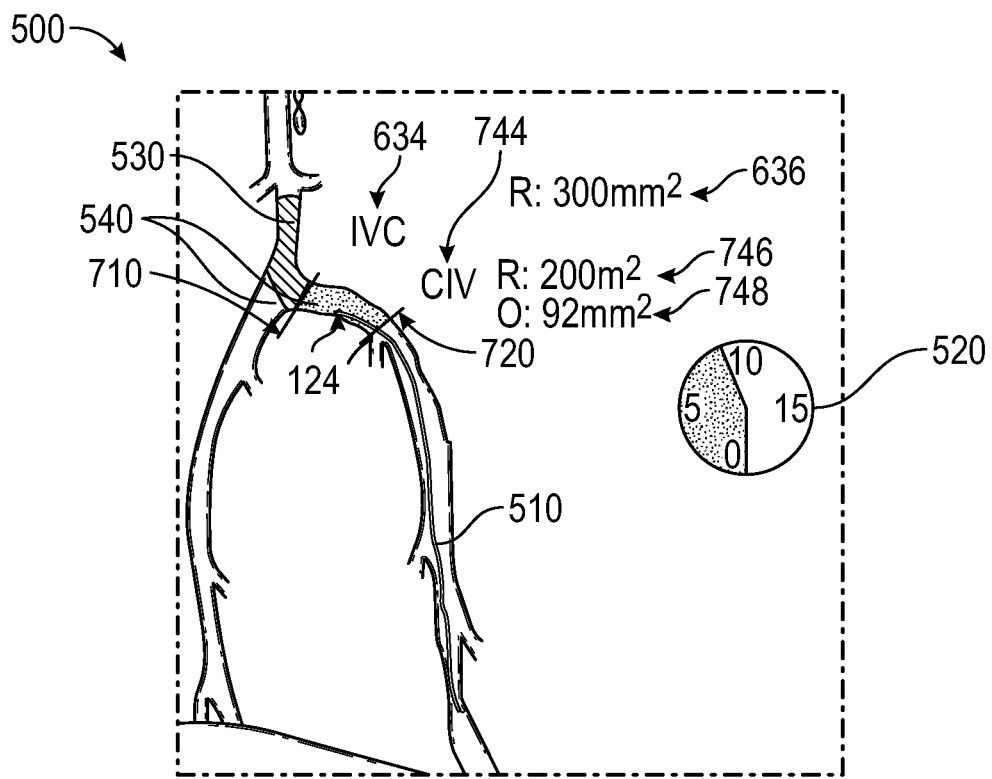
FIG. 7 illustrates the screen display of an exemplary virtual venogram after the transducer array at the end of the catheter has been moved into the right common iliac vein, in accordance with at least one embodiment of the present disclosure.

FIG. 7 illustrates the screen display of an exemplary virtual venogram 500 after the transducer array 124 at the end of the catheter 510 has been moved into the right common iliac vein 540, in accordance with at least one embodiment of the present disclosure. A text label 744 ("CIV") is provided adjacent to the vasculature to identify the segment occupied by the transducer array as the right common iliac vein 540. If the catheter were in the patient's left leg rather than the right leg as in this example, then the CIV 540 on the left half of the virtual venogram 500 would be labeled, and the CIV 540 on the right half of the virtual venogram 500 would be blank.

In this example, a reference value 746 and compression value 748 associated with the CIV segment 540 are automatically provided on the screen display as the transducer array 124 moves within the vasculature. For example, the compression value 748 may be a numerical value of the cross-sectional lumen area for the particular patient, or a % compression value. In that regard, the compression value is automatically calculated based on the obtained IVUS data and then output to the screen display adjacent to the virtual venogram 500. In this example, the CIV segment 540 is colored based on the comparison between the reference value and the compression value. Also visible are two position indicators 710 and 720, marking the boundaries of the CIV segment 540. As the pullback continues and the catheter 510 is withdrawn downward (i.e., distally or toward the patient's foot in this example) through the vasculature, the transducer array 124 will eventually cross position indicator 720, and the transducer array 124 will no longer be in the CIV segment 540.

In this example, the speed indicator 520 may be colored green, to indicate that the pullback speed is within the desired range.

Figure 8:
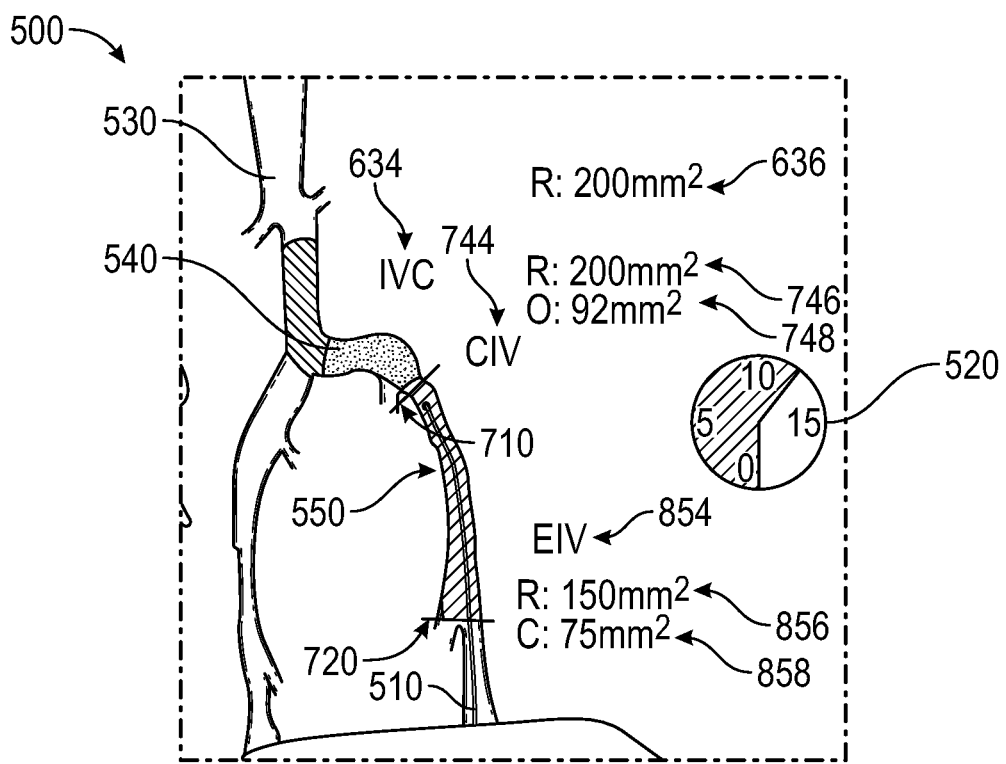
FIG. 8 illustrates the screen display of an exemplary cartoon roadmap or virtual venogram after the transducer array at the end of the catheter has been moved into the right external iliac vein, in accordance with at least one embodiment of the present disclosure.

FIG. 8 illustrates the screen display of an exemplary cartoon roadmap or virtual venogram 500 after the transducer array 124 at the end of the catheter 510 has been moved into the right external iliac vein 550, in accordance with at least one embodiment of the present disclosure. A text label 854 ("Hy") is provided adjacent to the vasculature to identify the segment occupied by the transducer array 124 as the external iliac vein. The reference value 856 and compression value 858 associated with the EIV segment are automatically provided and/or calculated. The EIV segment 550 is colored differently than the IVC and CIV segments 530 and 540, based on the comparison between the reference value 856 and the compression value 858. For example, when the compression value is equal to or greater than 50% of the reference value, the EIV segment can be colored in a third color (e.g., red) to indicate that the amount of compression is potentially harmful to the patient.

FIG. 8 also illustrates the speed gauge 520 indicating that the pullback speed is too high. In that regard, a greater proportion of the speed gauge is colored (compared to e.g., FIGS. 5-7) to show a higher pullback speed. In this example, the speed gauge 520 is colored red to provide real time feedback to the user that the pullback speed should be slowed. Also visible are the position markers 710 and 720, now marking the proximal and distal boundaries of the EIV segment 550.

Figure 9:
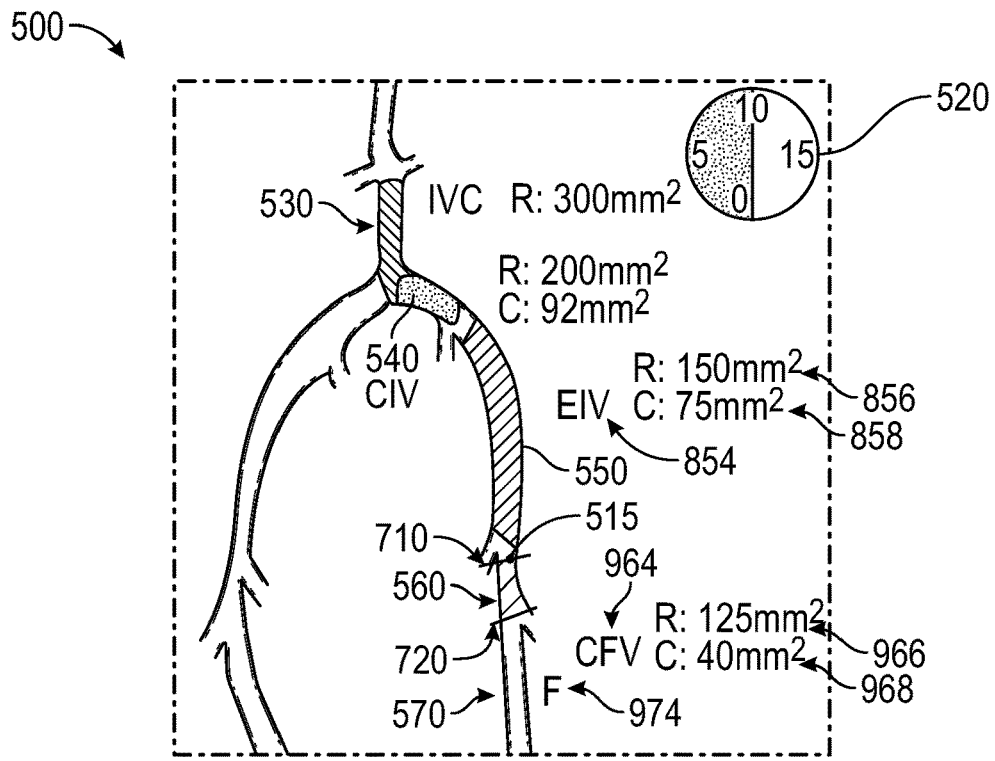
FIG. 9 illustrates the screen display of an exemplary virtual venogram after the transducer array at the end of the catheter has been moved into the right common femoral vein, in accordance with at least one embodiment of the present disclosure.

FIG. 9 illustrates the screen display of an exemplary virtual venogram 500 after the transducer array 124 at the end of the catheter 510 has been moved into the right common femoral vein 560, in accordance with at least one embodiment of the present disclosure. The vasculature segments have been sequentially highlighted ion the virtual venogram 500 as the transducer array passes through them. A text label 964 ("CFV") is provided adjacent to the vasculature to identify the segment occupied by the transducer array 124 of the catheter 510 as the common femoral vein 560. The reference value 966 and compression value 968 associated with the CFV segment 560 are automatically provided and/or calculated. The CFV segment 560 is colored differently than the IVC, CIV, and EIV segments, based on the comparison between the reference value and the compression value. For example, when the compression value is greater than 50% of the reference value, the segment 560 can be colored in a fourth color (e.g., yellow) to indicate that the amount of compression is not harmful to the patient.

Also visible are the position indicators 710 and 720, now marking the proximal and distal boundaries of the right CFV segment 560. In this example, the right femoral vein 570 also has a label 974 ("F"), although no reference value, compression value, or color are displayed, as the transducer array 515 has not yet been pulled back into the right F segment 570.

In this example, the speed indicator 520 may be colored green, to indicate that the pullback speed is within the desired range.

Figure 10:
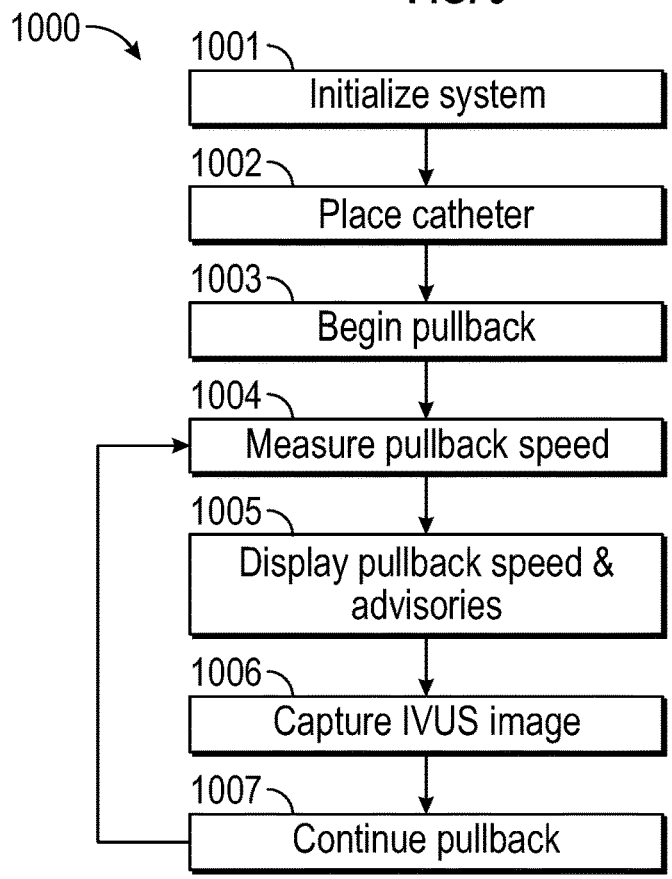
FIG. 10 illustrates a flow diagram showing the method followed by the pullback speed management system.

FIG. 10 illustrates a flow diagram showing the method 1000 followed by the pullback speed management system. In step 1001, a user enters initialization data, if any, into the system. Such data may include, but is not limited to, information about the procedure type, disease type, entry point into the patient's vasculature, direction of travel, or limb or other body part to be studied. In step 1002, the clinician moves the imaging probe or ultrasound transducer array 124 of the catheter 102 into position, e.g., advanced through a vessel or lumen to the point where a pullback procedure can begin. In some embodiments, this is done by the clinician without assistance from the system. In other embodiments, the system may provide instructions to the clinician. In step 1003, the clinician or other user indicates to the system that the recording process can begin. This may be done for example by activating a RECORD button on a touchscreen. The clinician then begins moving the catheter (e.g., by pulling the catheter back through the vasculature of interest), and the system captures a sufficient number of initial frames (e.g., at least two initial frames) to begin performing speed calculations. In step 1004, the system, operating on the processor 106, measures the pullback speed of the catheter using image analysis and a machine learning or pattern recognition algorithm to observe the frame-to-frame changes in the IVUS image over the past several frames (e.g., the past 10 or 100 frames) such as vessel taper rates and the passage of branching vessels and other anatomical landmarks and anatomical features for the area under investigation. Based on the dimensions of representative anatomy for a generic human, a demographic group, or a particular patient, the frame rate (i.e., a known time interval between successively captured images) can be used to deduce the longitudinal translation velocity or pullback speed of the imaging probe in real time or near-real time. In an example, the ideal pullback speed is between 2 mm/sec and 5 mm/sec. If insufficient frames have been gathered thus far to produce a speed calculation, the speed is not calculated.

In step 1005, the method 1000 displays a representation of the pullback speed (e.g., speed indicator 520, as shown for example in FIGS. 5-9), if available, on the monitor 108. The system may additionally display advisories to the user indicating whether the pullback speed is too high or too low, i.e., whether it should be increased or decreased such that it falls within a specified optimal range for capturing clear images (e.g., IVUS images). In step 1006, the next image is captured by the imaging catheter 102, and in step 1007, execution of the method returns to step 1004, with the newly captured image now part of the growing dataset used to determine the pullback speed. Execution continues to loop between 1004 and 1007 as shown, until interrupted by the user (e.g., by activating a STOP or EXIT control).

Examples of border detection, image processing, image analysis, and/or pattern recognition include U.S. Pat. No. 6,200,268 entitled "VASCULAR PLAQUE CHARACTERIZATION" issued Mar. 13, 2001 with D. Geoffrey Vince, Barry D. Kuban and Anuja Nair as inventors, U.S. Pat. No. 6,381,350 entitled "INTRAVASCULAR ULTRASONIC ANALYSIS USING ACTIVE CONTOUR METHOD AND SYSTEM" issued Apr. 30, 2002 with Jon D. Klingensmith, D. Geoffrey Vince and Raj Shekhar as inventors, U.S. Pat. No. 7,074,188 entitled "SYSTEM AND METHOD OF CHARACTERIZING VASCULAR TISSUE" issued Jul. 11, 2006 with Anuja Nair, D. Geoffrey Vince, Jon D. Klingensmith and Barry D. Kuban as inventors, U.S. Pat. No. 7,175,597 entitled "NON-INVASIVE TISSUE CHARACTERIZATION SYSTEM AND METHOD" issued Feb. 13, 2007 with D. Geoffrey Vince, Anuja Nair and Jon D. Klingensmith as inventors, U.S. Pat. No. 7,215,802 entitled "SYSTEM AND METHOD FOR VASCULAR BORDER DETECTION" issued May 8, 2007 with Jon D. Klingensmith, Anuja Nair, Barry D. Kuban and D. Geoffrey Vince as inventors, U.S. Pat. No. 7,359,554 entitled "SYSTEM AND METHOD FOR IDENTIFYING A VASCULAR BORDER" issued Apr. 15, 2008 with Jon D. Klingensmith, D. Geoffrey Vince, Anuja Nair and Barry D. Kuban as inventors and U.S. Pat. No. 7,463,759 entitled "SYSTEM AND METHOD FOR VASCULAR BORDER DETECTION" issued Dec. 9, 2008 with Jon D. Klingensmith, Anuja Nair, Barry D. Kuban and D. Geoffrey Vince, as inventors, the teachings of which are hereby incorporated by reference herein in their entirety.

Figure 11A:
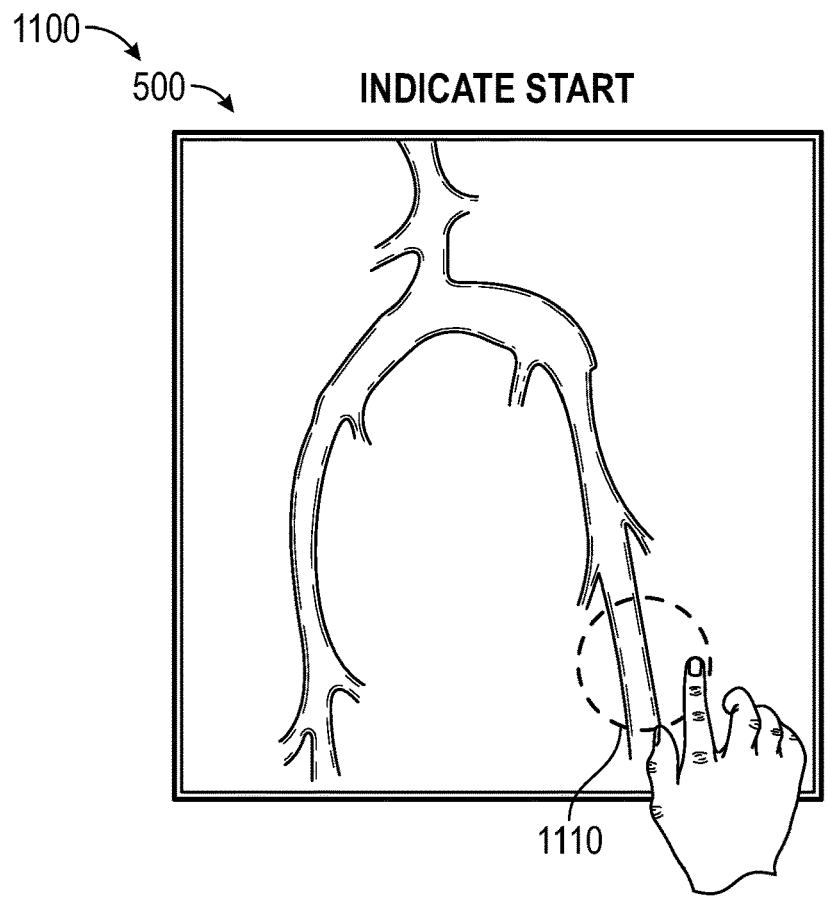
FIG. 11A illustrates a screen display of a virtual venogram at the start of a pullback procedure, in accordance with at least one embodiment of the present disclosure.
Figure 11B:
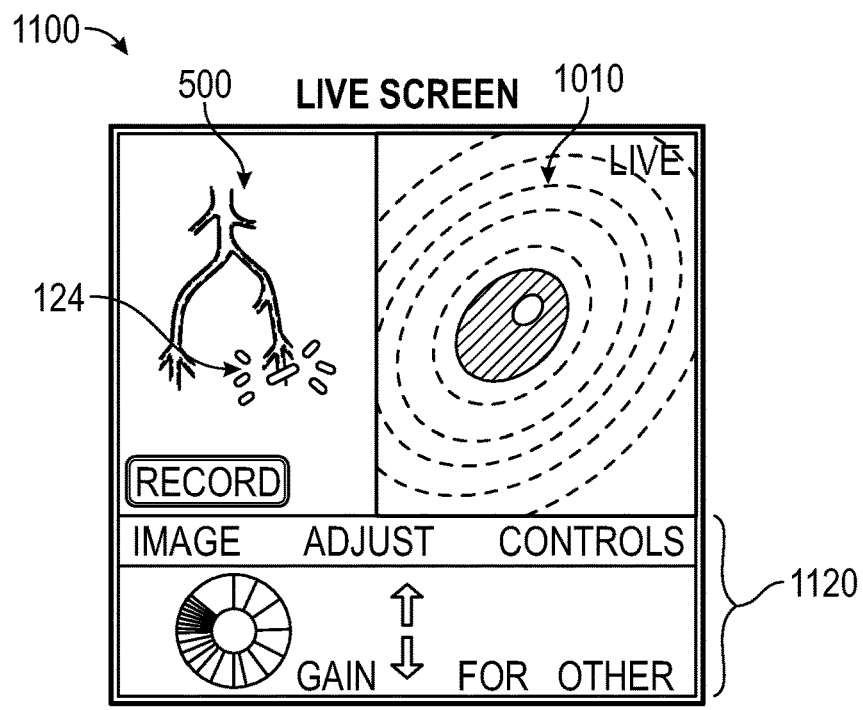
FIG. 11B illustrates screen display of a live view during a pullback procedure in accordance with at least one embodiment of the present disclosure.
Figure 12:
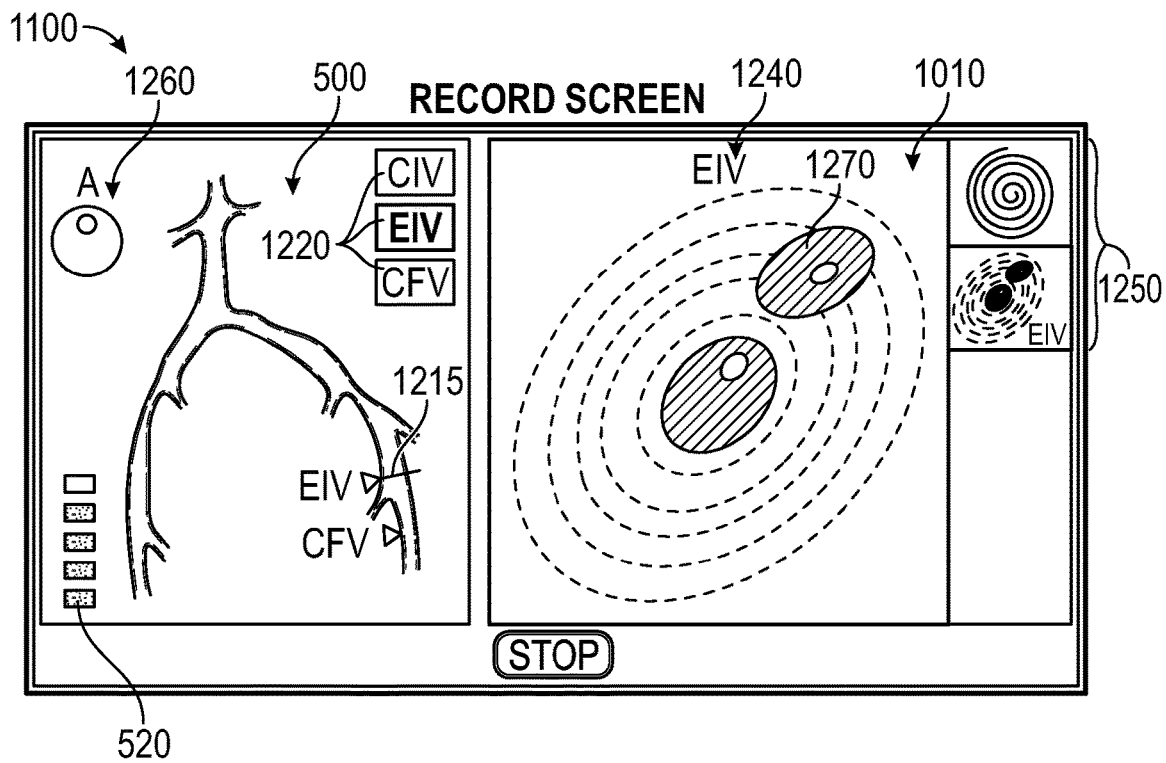
FIG. 12 illustrates a screen display during pullback, e.g., during recording of the IVUS data, in accordance with at least one embodiment of the present disclosure.

FIGS. 11-12 illustrate screen displays providing the user guidance during and after a IVUS pullback in peripheral vasculature. The screen displays provide: auto-label based on arterial information, auto-label based on image analysis, bookmark thumbnails on the side, roadmap view (cartoon), segment mapping, longitudinal and compression indicator, auto-label on all relevant parts, user selected access point, image adjustment, and pullback speed indicator.

FIG. 11A illustrates a screen display 1100 of a virtual venogram at the start of a pullback procedure, in accordance with at least one embodiment of the present disclosure. As shown by a start indicator 1110, the user indicates where on anatomy he or she is starting the pullback on the graphical view of vasculature displayed in the virtual venogram 500. This information serves as an input to the IVUS pullback venogram system, to aid in automatically identifying the different vein segments 530, 540, 550, 560, and 570 as the IVUS transducer array 124 passes through them, and in automatically deducing the speed of pullback for the transducer array 124 through the different vein segments, via image recognition.

FIG. 11B illustrates screen display 1100 of a live view during a pullback procedure in accordance with at least one embodiment of the present disclosure. A virtual venogram 500, acting as a roadmap in the live view 1100, provides a longitudinal view of anatomical structures surrounding the transducer array 124, and automatically shows where the transducer array 124 is located within the body. In some embodiments, a co-registered X-ray, CAT scan, or fluoroscopy image may be used as a roadmap instead of or in addition to the virtual venogram 500. Aspects of co-registration are described, for example, in U.S. Pat. Nos. 7,930, 014 and 8,298,147, the entireties of which are hereby incorporated by reference in its eternity. The screen display 1100 also includes a live tomographic IVUS image 1010. In addition, the screen display 1100 includes image setting controls 1120 (e.g., gain, field of view, etc.).

FIG. 12 illustrates a screen display 1100 during pullback, e.g., during recording of the IVUS data, in accordance with at least one embodiment of the present disclosure. A current frame indicator 1215 shows where on the cartoon roadmap or virtual venogram 500 of the vasculature the transducer array 124 of the catheter 510 is presently located. Label presets 1220 are also provided (e.g., vasculature segment abbreviations such as CIV, EIV, CFV, etc.). The IVUS frames are automatically labeled based on image analysis. In this example, the current position of the transducer array has been identified as the exterior iliac vein (e.g., the external iliac vein 550 of FIG. 5), and so the EIV label preset 1220 is highlighted or illuminated. A pullback speed indicator 520 provides guidance to the clinician or other user for a stable pullback speed. The pullback speed indicator 520 can be a series of blocks that are filled based on the speed (e.g., more blocks indicate faster speed and fewer blocks indicate slower speed). A tomographic IVUS image 1010 shows the current frame, and an automatic label 1240 can be generated using image analysis with the label presets described with respect to the current frame indicator 1215, e.g., by the vasculature segment abbreviation. Bookmark thumbnails 1250 appear when the user presses the bookmark option and/or the label preset option. A direction indicator 1260 is also included, showing, e.g., the orientation or direction of movement of the transducer array. Anterior (A), posterior (P), medial (M), lateral (L), and/or other suitable direction labels can be used. The direction indicator can include a compass arrow that moves based on the direction of movement. Interesting anatomy 1270 (e.g., compression or thrombus) within the IVUS image 1010 can be colored, shaded, and/or highlighted.

Figure 13:
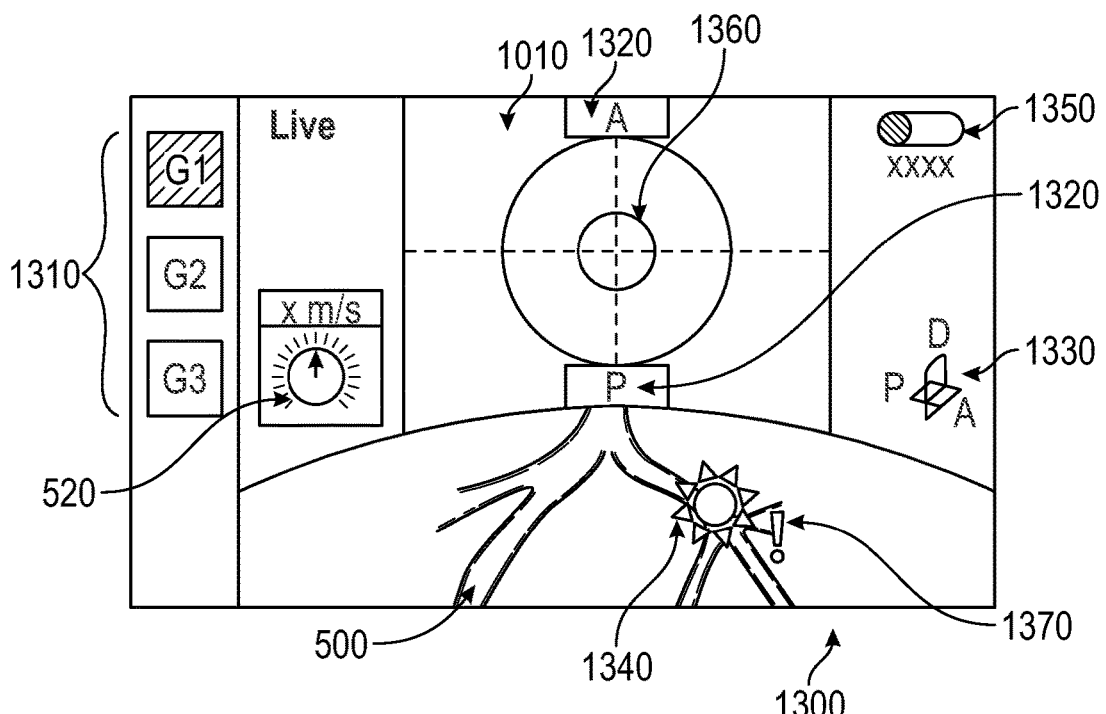
FIG. 13 illustrates a screen display associated with navigating the IVUS imaging catheter to a suggested location (e.g., a compression or blockage) in the vasculature.
Figure 14:
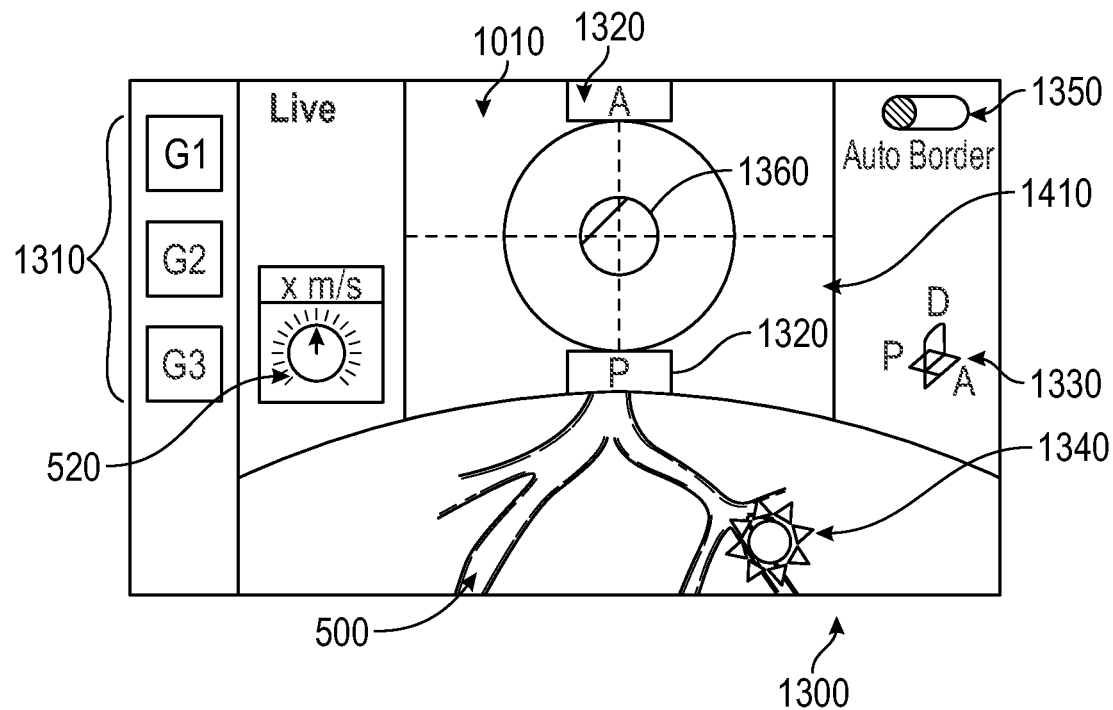
FIG. 14 illustrates a screen display once the IVUS imaging catheter has been brought to the suggested compression in the vasculature.
Figure 15:
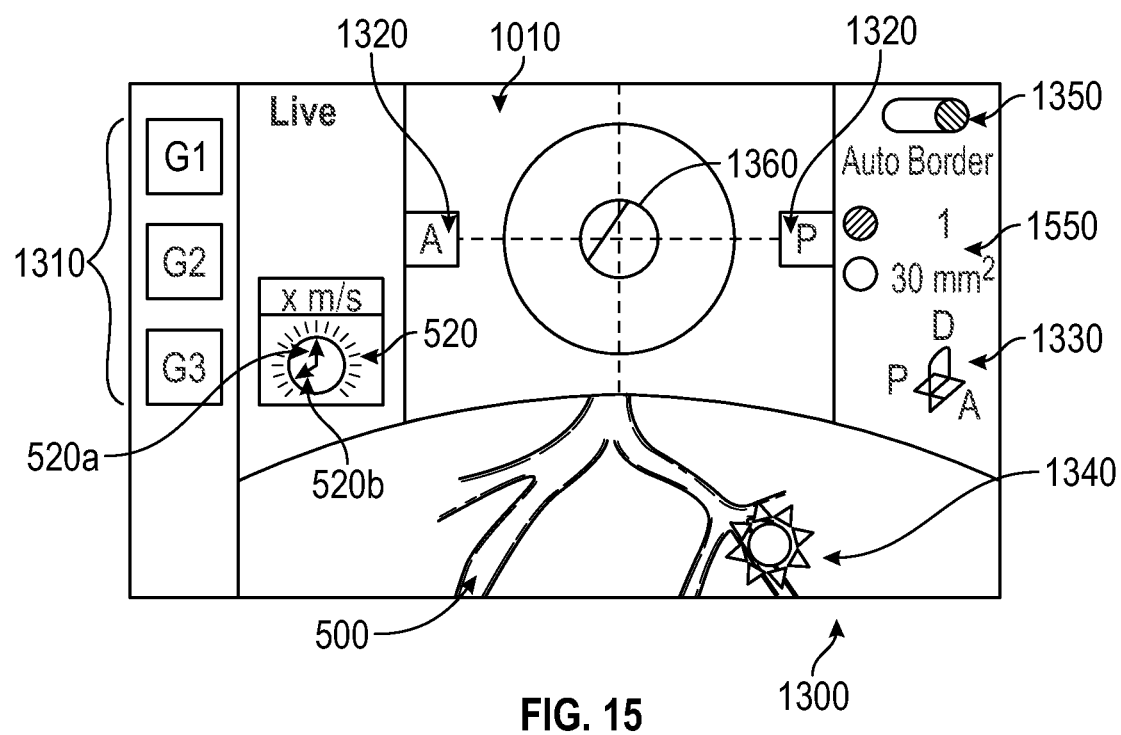
FIG. 15 illustrates a screen display with an auto-border toggle turned on by the user.

FIGS. 13-15 illustrate screen displays providing the user guidance during an IVUS pullback in peripheral vasculature. The screen displays advantageously support the physician or user to navigate to an area of interest. The screen displays provide: suggested compression area, navigation support, anterior vs. posterior orientation, on demand automatic border detection and display, automatic border detection and display upon reaching destination (e.g., desired area of interest, and pullback speed indication). FIGS. 13-15 can be displayed as part of navigation during live IVUS.

FIG. 13 illustrates a screen display 1300 associated with navigating the IVUS imaging catheter 102 to a suggested location (e.g., a compression or blockage) in the vasculature. The screen display can include a choice of image settings (e.g., filters) 1310 (e.g., labeled "G1", "G2", "G3", etc.). The filters can be preset image settings (e.g., grey scale, contrast, gain, focus, and/or other image settings) for display of the tomographic IVUS image. In this example, the first image setting 1310 ("G1") has been selected.

A live tomographic IVUS image 1010 of a vessel 1360 is shown in the top middle portion of the screen display. Direction markers 1320 (in this example, "A" for anterior and "P" for posterior) are provided with the IVUS image to provide orientation information about the IVUS image 1010. The right side of the screen display also includes an anatomical plane indicator 1330 to provide additional orientation information about the IVUS image and/or where the catheter is currently located, what direction it is moving, etc. A roadmap image 500 of the vasculature (e.g., an angiographic image, venographic image, or virtual venogram) is displayed in the bottom middle portion of the screen display. A marker 1340 indicative of the current location of the catheter (e.g., the location of the transducer array 124) is shown in the roadmap image (e.g., a flashing circle or circle with rays around it). In some embodiments, this location is determined automatically from the images captured by the imaging catheter 102. In other embodiments, the location is determined through image analysis of an external image captured by the external imaging system 132. A marker 1370, indicative of the suggested compression location to be evaluated, is also shown on the roadmap image 500 (e.g., the medal shape, representing the destination or finish line). The markers 1340 and 1370 allow the user to visually evaluate the distance the catheter is from the suggested target area. In this example, an auto-border toggle 1350 is provided at the top right of the screen display 1300.

A speed indicator 520, such as a speed gauge, is also provided on the left side of the screen display to show pullback speed. The speed indicator 520 may resemble an automotive speedometer, e.g., by including an arrow or needle indicating the current movement rate. A region (e.g., a quadrant) of the speed gauge 520 can be highlighted, colored, or shaded, indicating the desired velocity. The speed indicator 520 can also provide a numerical value of the current speed and/or the recommended speed.

FIG. 14 illustrates a screen display 1300 once the IVUS imaging catheter 102 has been brought to the suggested compression in the vasculature. In that regard, the screen display provides feedback to the user that catheter 102 (e.g., the transducer array 124) is at the area of interest. For example, a colored, highlighted, and/or shaded border 1410 (e.g., colored orange) may be provided around the tomographic IVUS image 1010 of the vessel 1360 to indicate that IVUS image 1010 is of the area of interest. Color, highlighting, and/or shading can be provided for current location marker 1340 (and/or for the rays around the marker) on the roadmap image 500, such as an orange color, indicating that the current location of the IVUS catheter transducer array 124 is at the region of interest. In that regard, the color of the current location marker 1340 (and/or rays or other emphasis around the marker 1340) in FIG. 13 is different (e.g., black) than the than color of the current location marker (and/or the rays or other emphasis around the marker, e.g., red) in FIG. 14. This is because the current location marker in FIG. 13 shows that the IVUS catheter is spaced from the area of interest (indicated by the medal shaped marker in FIG. 13), whereas the IVUS transducer array 124 is at the area of interest in FIG. 14.

Also visible in FIG. 14 are the image settings 1310, direction markers 1320, anatomical plane indicator 1330, auto-border toggle 1350, and speed indicator 520.

FIG. 15 illustrates a screen display 1300 with the auto-border toggle 1350 turned on by the user. The processing system 106 can execute algorithm(s) to perform image analysis, such as to automatically determine the boundary of the lumen 1360 in the tomographic IVUS image 1010. A measurement display 1550 shows an automatically calculated cross-sectional lumen area and/or lumen diameter, either or both of which can be calculated based on the determined boundary of the lumen. The calculated measurement or measurements 1550 can be displayed on, e.g., the right side of screen display, adjacent to the IVUS image. The direction markers 1320 (e.g., marking the A and P or anterior and posterior directions) can be reoriented as needed to provide orientation information about the IVUS image 1010. For example, the direction markers 1320 are provided at the left and right of the IVUS image in FIG. 15, in contrast to the top and bottom of the IVUS image in FIGS. 13 and 14. The speed indicator 520 shown in FIG. 15 can include two arrows 520*a* and 520*b* on the gauge. For example, one arrow can indicate the current pullback speed, while the other arrow can indicate the recommended pullback speed. The arrows 520*a* and 520*b* can be visually differentiated by coloring, shading, highlighting, style, etc.

Also visible in FIG. 15 are the roadmap image 500, image settings 1310, anatomical plane indicator 1330, position marker 1340, and shaded border 1410.

FIGS. 16*a*-16*d* provide various examples of speed indicators 520 providing feedback to the user about the pullback rate of the IVUS catheter 102. The speed indicators 520 can be provided adjacent to or proximate to the roadmap image

Figure 16A:
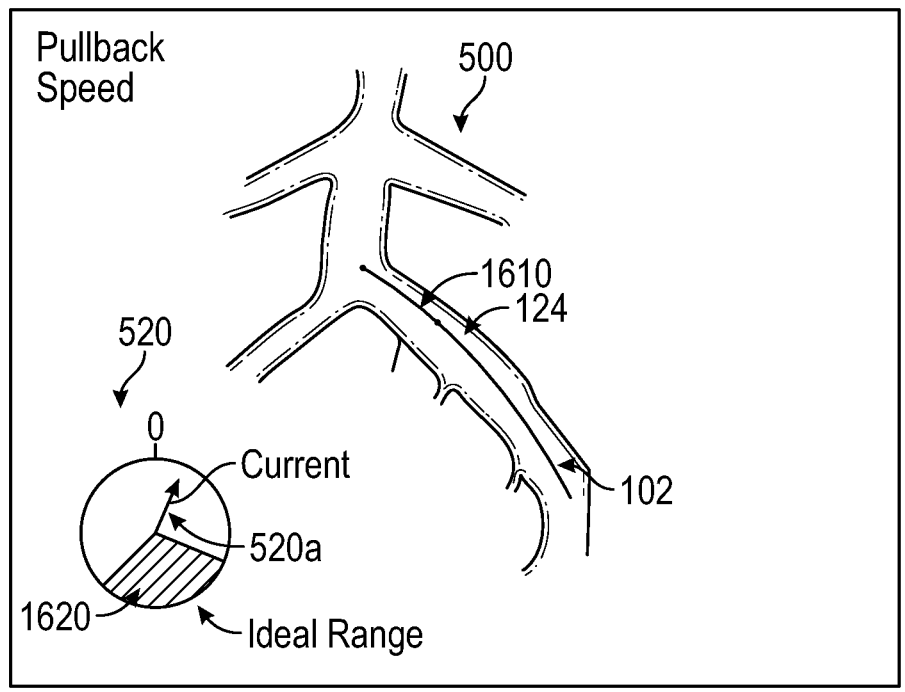
FIGS. 16a-16d provide various examples of speed indicators providing feedback to the user about the pullback rate of the IVUS catheter.
Figure 16B:
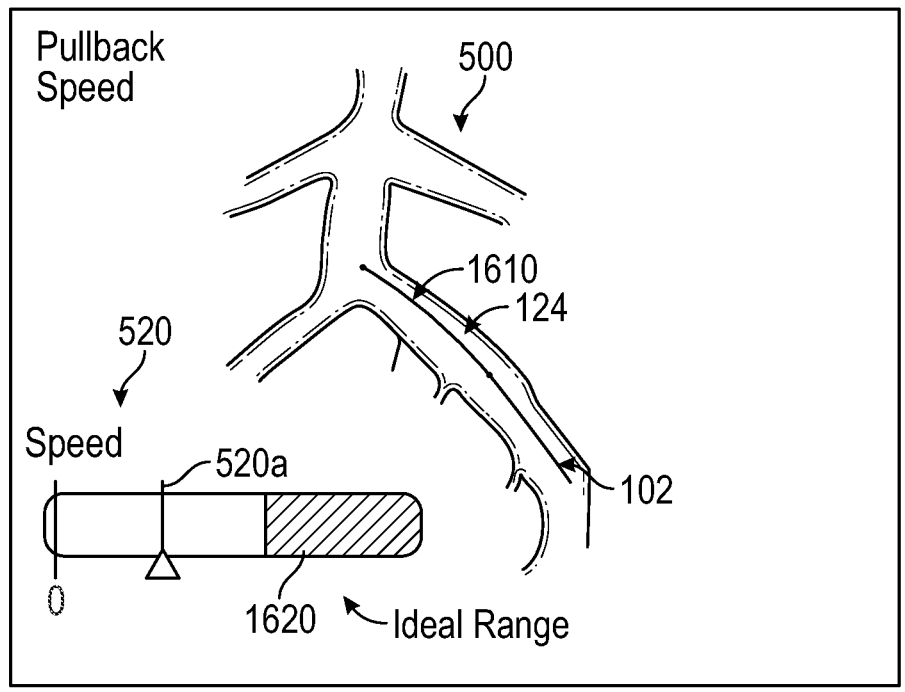
Figure 16C:
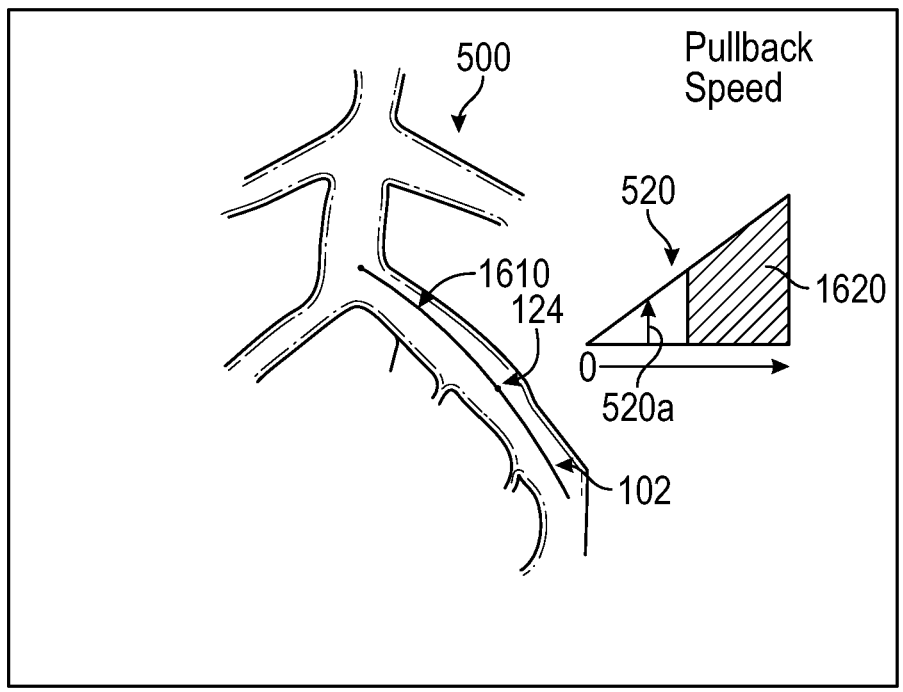
Figure 16D:
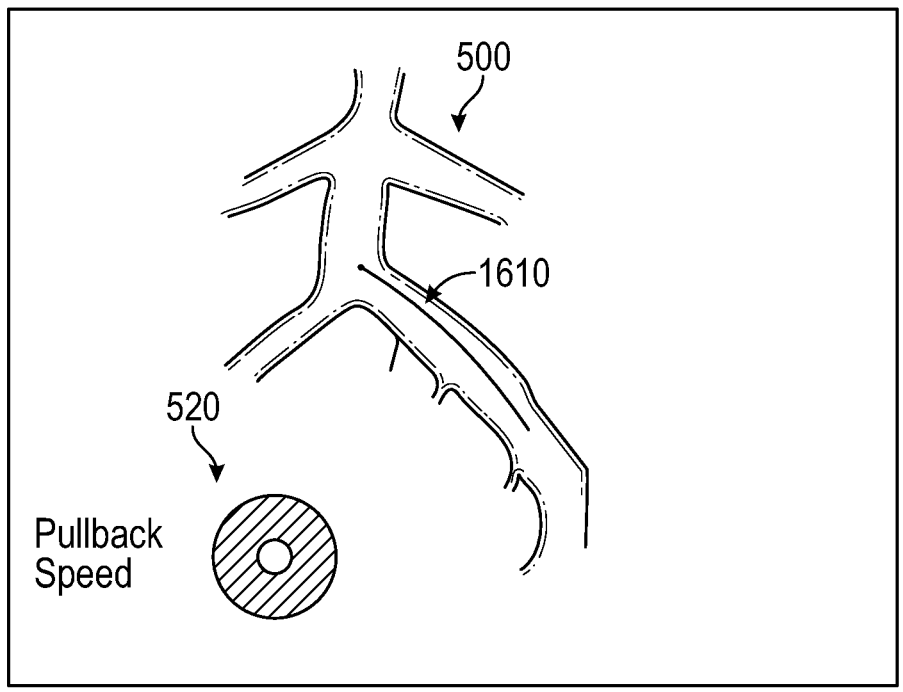

500. FIG. 16*a* illustrates a circular speed gauge 520 with a zero value at the 12 o'clock position. Larger speeds can be indicated in a clockwise direction. An arrow or needle 520*a* on the gauge 520 indicates the current speed. A wedge-shaped and/or pie-shaped region of the circular gauge is colored, highlighted, and/or shaded to show the ideal speed range 1620, which comprises a minimum ideal speed, a maximum ideal speed, and a range of speeds between the minimum and maximum ideal speeds. In that regard, speeds that are slower than and speeds that are faster than the ideal speed range 1620 may lead to improper collection of IVUS data, which can harm IVUS image quality. FIG. 16*b* illustrates a rectangular, bar-shaped speed gauge 520. The zero position is at the left edge of the gauge, with increasing values indicated to the right. A current speed is indicated by a marker 520*a* with a triangular base and an arm extending from the triangle transversely across the gauge. An ideal speed range 1620 is indicated in the gauge by a portion that is colored, highlighted, and/or shaded. FIG. 16*c* illustrates a triangular speed gauge 520. The zero position is at the left edge of the gauge 520, with increasing values indicated to the right. The height of the gauge 520 increases with increasing speed values to the right. An ideal speed range 1620 is indicated in the gauge by a portion that is colored, highlighted, and/or shaded. FIG. 16*d* shows an additional type of speed indicator 520, wherein a circular indicator grows and shrinks in proportion to the speed, and a donut-shaped shaded area indicates the desired speed range. If the borders of the circular indicator fall within the shaded donut, then the speed is within the desired range. If the borders of the circular indicator fall within the "hole" of the donut, then the speed is too low, and if they fall outside the outer edge of the donut, then the speed is too high. Too-high or too-low speeds may additionally be indicated by a color change.

Other types of speed indicators may be used instead of or in addition to those described above, including graphical, schematic, alphanumeric, voice, auditory tone, and tactile or haptic speed indicators. Also visible in FIGS. 16*a*-16*c* are the roadmap image 500, including representations of the catheter 102 and transducer array 124, along with a color-coded trail 1610 indicating past positions of the transducer array or sensor head 124 during the pullback. In an example the color of the trail 1610 indicates whether the pullback speed was too slow (e.g., red), too fast (e.g., yellow), or within the ideal range 1620 (e.g., green).

Figure 17:
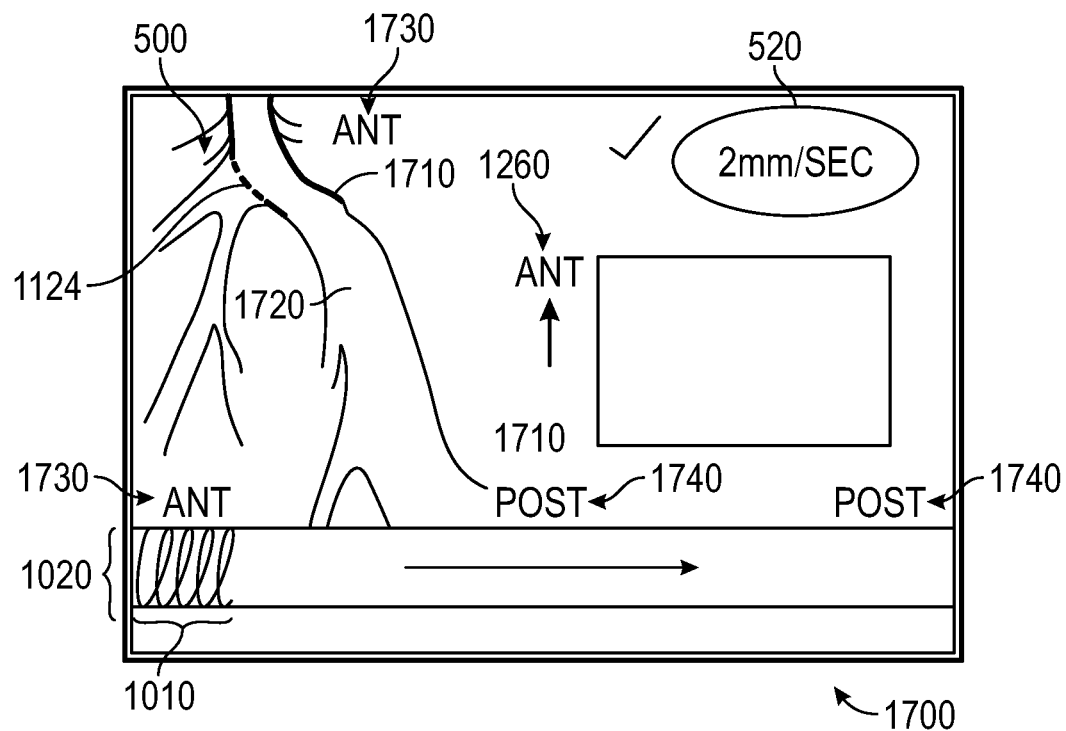
FIG. 17 illustrates a screen display during pullback, e.g., during recording of IVUS data, in accordance with at least one embodiment of the present disclosure.

FIG. 17 illustrates a screen display 1700 during pullback, e.g., during recording of IVUS data, in accordance with at least one embodiment of the present disclosure. On the left side of the screen display, a roadmap image, co-registered external image, or virtual venogram 500 of the vasculature is shown. A portion 1710 of the vasculature 1720 from which IVUS data has already been collected is highlighted, colored, and/or shaded. For example, the vessel boundary in the region 1710 where pullback has already occurred is bolded, while the other areas of the vessel 1720 are shown more lightly. A solid bold line 1710 can be used for the vessel boundary, while a dashed bold line 1124 can be used when crossing a branching vessel. More and more of the vessel 1720 is visually accentuated 1710 as the pullback progresses. In that regards, the map 500 of the vasculature 1720 is built during the pullback. The anterior (ANT) and posterior (POST) portions 1730 and 1740 of the vasculature are labeled on the roadmap image 500, with pullback occurring with the transducer array 124 being moved longitudinally from the anterior portion 1730 to posterior portion 1740. Along the bottom of the display, a horizontal ILD 1020 is shown. The ILD 1020 is formed from the IVUS data during the pullback. As shown, the ILD 1020 is also built during the pullback, with more and more IVUS image frames 1010 being added to the ILD 1020 as the pullback progresses. The anterior (ANT) and posterior (POST) portions 1730 and 1740 of the vasculature 1720 are labeled on the roadmap image 500. A compass 1260 is provided in the middle of the screen display 1700. For example, the anterior direction (ANT) can always be on top (e.g., the 12 o'clock position). The compass arrow 1260 can change directions based on the orientation or direction of movement of the transducer array within the vasculature 1720 during the pullback.

A pullback speed indicator 520 is provided on the top right of the screen display. The pullback speed indicator 520 can display the speed of the manual pullback with a numerical value. The indicator can also include a graphical representation (e.g., a symbol) of whether the speed is too fast, too slow, or correct. For example, a checkmark can indicate that the pullback speed is correct.

Figure 18:
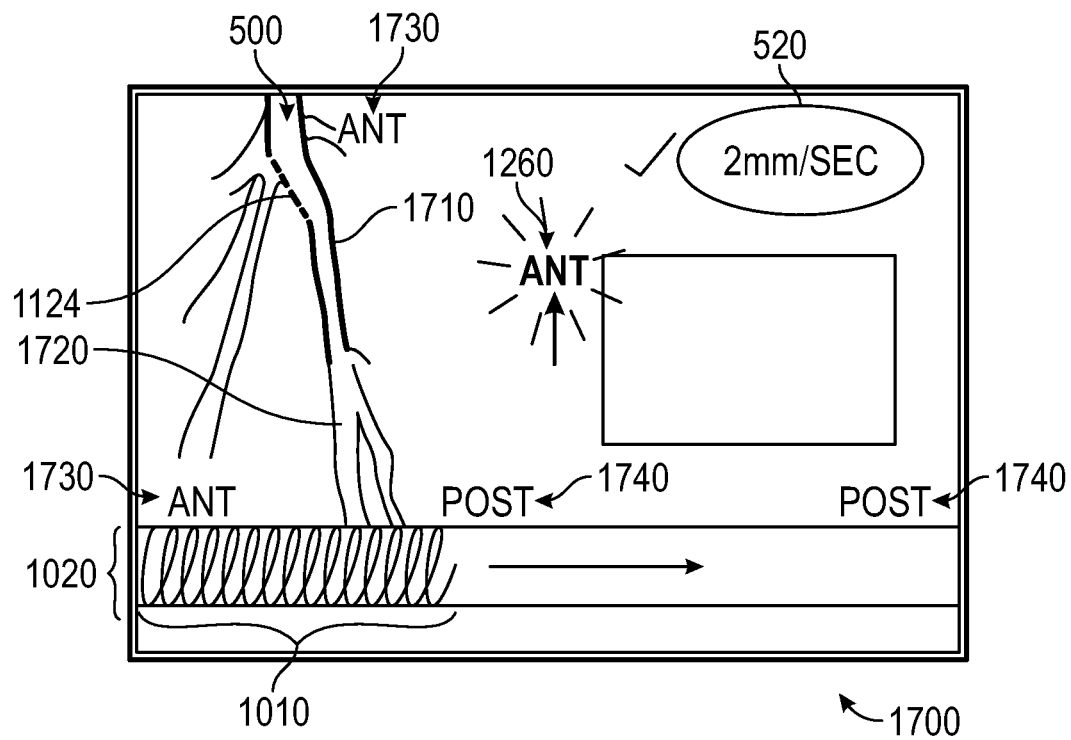
FIG. 18 illustrates an example screen display during a later stage of an IVUS pullback, in accordance with at least one embodiment of the present disclosure.

FIG. 18 illustrates an example screen display 1700 during a later stage of an IVUS pullback, in accordance with at least one embodiment of the present disclosure. As shown on the virtual venogram 500 of the left side of the screen display 1700, a greater length of the vasculature 1720 has been highlighted (1710, 1124) as compared to FIG. 17, indicating that IVUS data has been obtained from a greater length of the vasculature 1720. Similarly, a greater length of the ILD 1020 has been filled in with the obtained IVUS image frames 1010. The direction label (ANT) of the compass 1260 or the arrow of the compass 1260 can blink when the computer or processor is unsure of the direction the transducer array 124 is moving or oriented within the vasculature, or when the direction/orientation is being recalculated.

Figure 19:
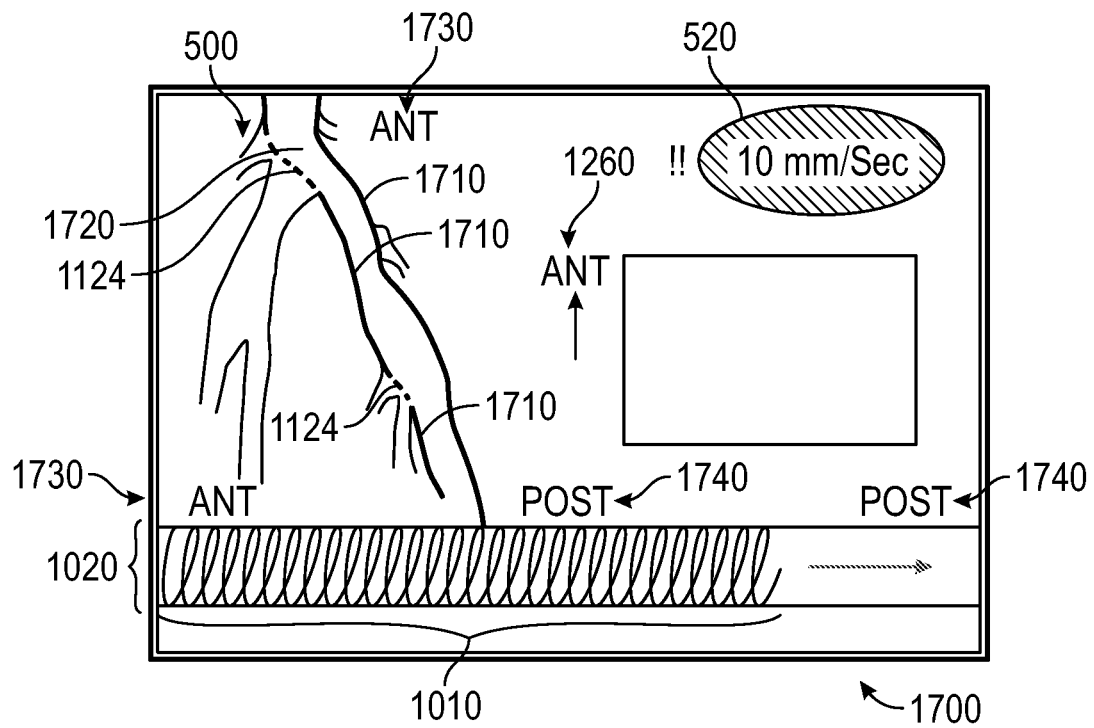
FIG. 19 illustrates an example screen display at or near the end of the IVUS pullback, in accordance with at least one embodiment of the present disclosure.

FIG. 19 illustrates an example screen display 1700 at or near the end of the IVUS pullback, in accordance with at least one embodiment of the present disclosure. As shown on the virtual venogram 500 at the left side of the screen display 1700, all or nearly all of the length of the vasculature 1720 under investigation has been highlighted (1710, 1124), indicating that IVUS data 1010 has been obtained from almost the complete length. Similarly, all or nearly all of the length of the ILD 1020 has been filled in with the obtained IVUS image frames 1010.

The pullback speed indicator 520 on the top right of the screen display 1700 shows that the pullback speed is too high. For example, symbols (e.g., exclamation marks) and/or coloring (e.g., red) of the numerical speed value can be used to indicate to the user that the pullback speed should be slowed down.

Figure 20A:
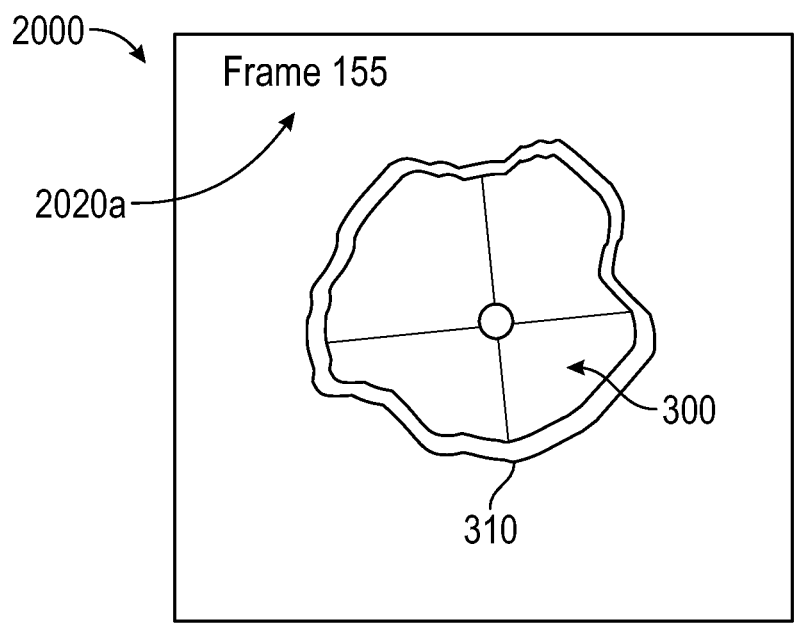
FIG. 20a illustrates a tomographic intraluminal image of a vessel with a vessel wall.

FIG. 20*a* illustrates a tomographic intraluminal image (e.g., an IVUS image) 2000 of a vessel 300 with a vessel wall 310. Also visible is a frame number 2020*a*.

Figure 20B:
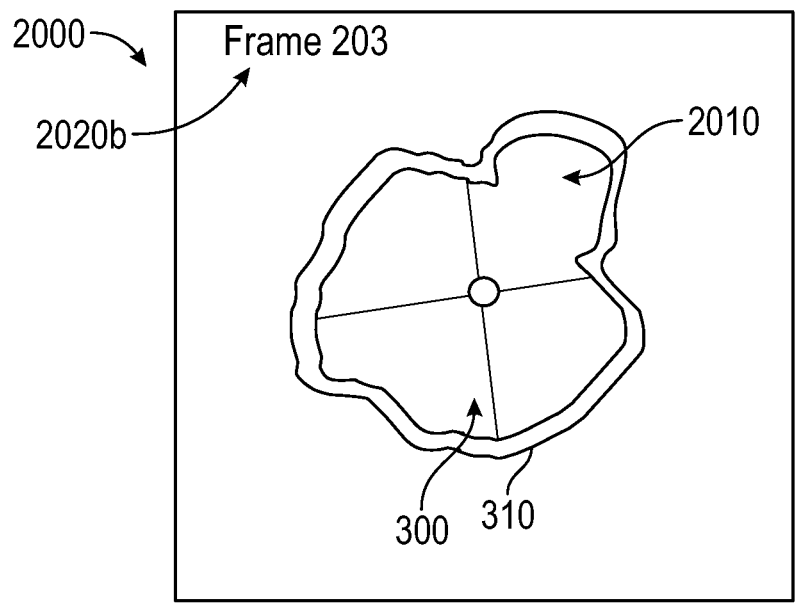

FIG. 20*b* illustrates a tomographic intraluminal image (e.g., an IVUS image) 2000 of a vessel 300 with a vessel wall 310 that is farther along the pullback than the image in FIG. 20*a*, as shown by the larger frame number 2020*b*. In this image, a branching vessel 2010 beginning to bud off from the vessel 300.

Figure 20C:
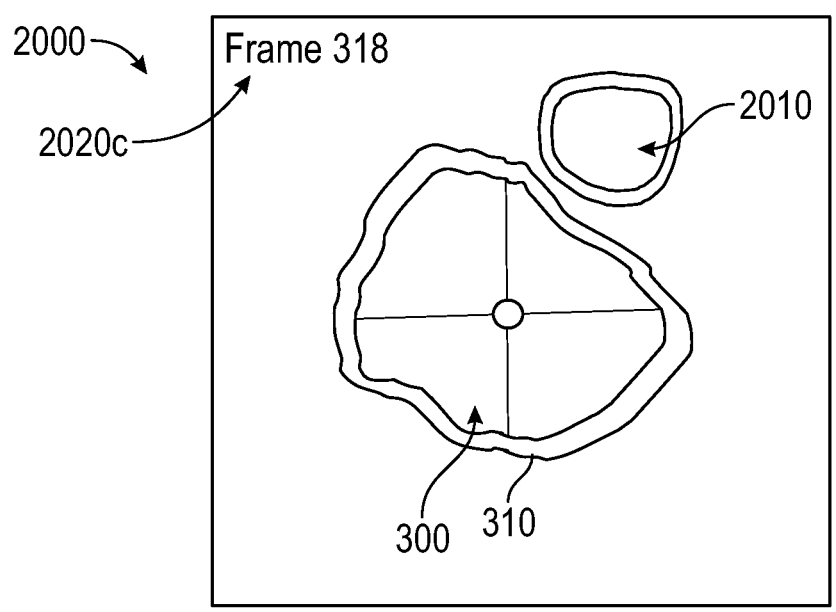
FIG. 20c illustrates a tomographic intraluminal image of a vessel with a vessel wall that is farther along the pullback than the image in FIG. 20b.

FIG. 20*c* illustrates a tomographic intraluminal image (e.g., an IVUS image) 2000 of a vessel 300 with a vessel wall 310 that is farther along the pullback than the image in FIG. 20*b*, as shown by the larger frame number 2020*c*. In this image, the branching vessel 2010 has fully separated from the vessel 300. Since the frame rate is known (e.g., 12 fps or 30 fps), the passage of branching vessels 2010 or other anatomical landmarks can be associated with the physical dimensions of reference anatomy for a generic human body, for a representative demographic group, or known patient anatomy. Thus, the rate of change of anatomical landmarks from one frame to the next (and especially over a plurality of frames) can be used to deduce the speed of the intraluminal probe 102 through the vessel 300.

Figure 21A:
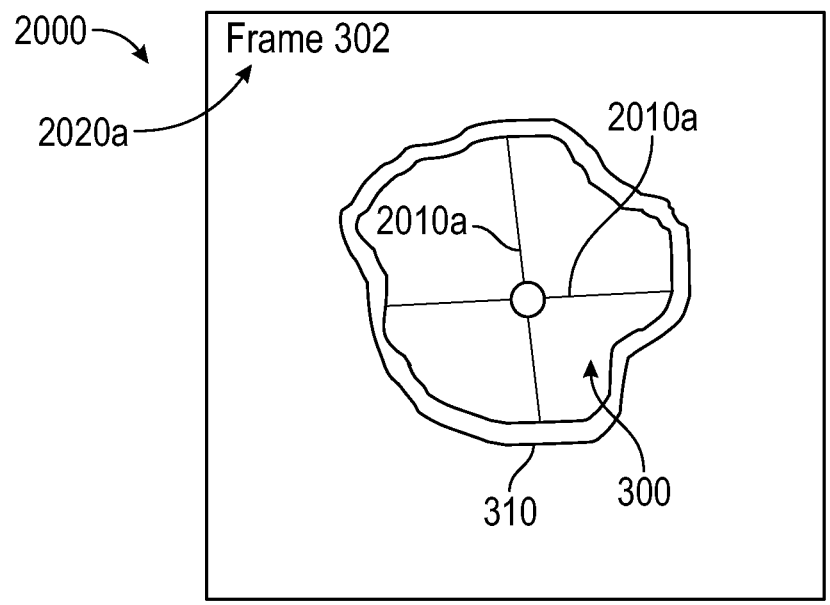
FIG. 21a illustrates a tomographic intraluminal image of a vessel with a vessel wall.

FIG. 21a illustrates a tomographic intraluminal image (e.g., an IVUS image) 2000 of a vessel 300 with a vessel wall 310. Diameter measurements 2010a show the width of the vessel, from which a cross-sectional area can be determined. Also visible is a frame number 2020a.

Figure 21B:
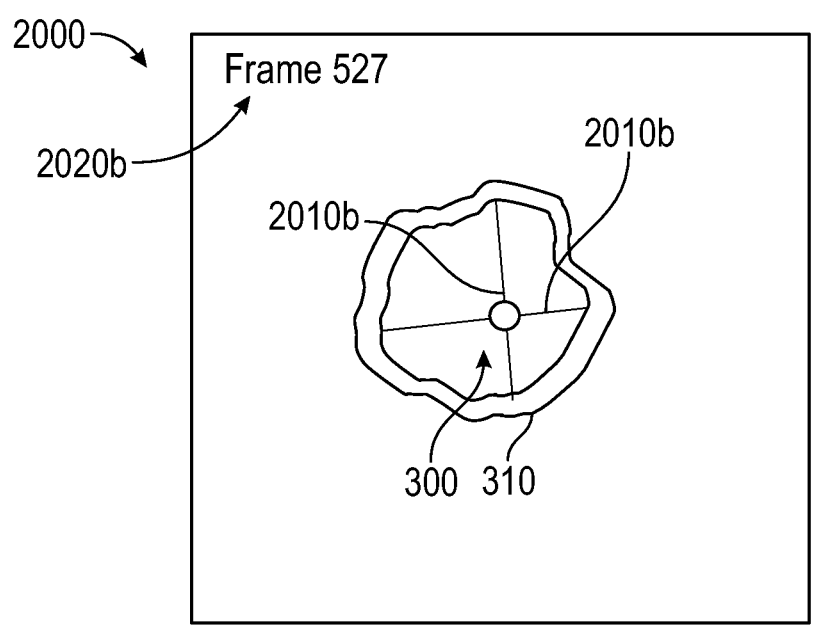

FIG. 21b illustrates a tomographic intraluminal image (e.g., an IVUS image) 2000 of a vessel 300 with a vessel wall 310 that is farther along the pullback than the image in FIG. 20a, as shown by the larger frame number 2020b. In this image, the vessel diameter and cross-sectional area are smaller. The frame rate of the intraluminal imaging system 100 can then be associated with known vessel taper rates for the target vessel in a generic human body, or a representative demographic group, or known patient anatomy. Thus, the rate of change of vessel diameter or area from one frame to the next (and especially over a plurality of frames) can be used to deduce the speed of the intraluminal probe 102 through the vessel 300.

During IVUS pullback, the user is pulling (or pushing) the catheter across the vessel lumen to be able to capture IVUS images. Currently, many IVUS catheter for Peripheral Vascular interventions (e.g., PV 0.014, PV 0.018, and PV 0.035 catheters from Philips Volcano) support only phased array technology, with no control on speed over the pullback. To be able to guide physicians to reach and keep the constant speed while doing pullback, a 'speed indicator' in included on the IVUS screen, as shown in, e.g., FIGS. 6, 7, 9, 11, 13, 14, and 16-19. The speed indicator shows the IVUS operator its actual speed within the vessel. The speed indicator can be activated during the record phase (e.g., after the user selects the record button to store the IVUS data, such as at the beginning of the pull back). The speed indicator communicates to the operator when the speed in not in the right range to ensure adequate pullback recording and suggests the right speed range. As shown in FIGS. 8, 9, 13, 15, and 19, a too fast/slow velocity can be suggested by color coding. Speed indicator and color coding can guide physicians to perform a steady pullback throughout the whole vessel. The speed indicator can provide a measure of velocity or account for any way to communicate to the user the correct range of speed to reach and keep during pullback. Different representations for speed indicator while doing pullback are contemplated (e.g., speed indicator like in cars, with quadrant indicating current movement rate and desired velocity as in FIG. 16a, and/or speed indicator through colors and square bars as in FIG. 16b). Thanks to this constant velocity, a rough estimation of pullback length can be derived, this being extremely valuable for physicians to decide upon stent length right after pullback and measurement review.

Figure 22:
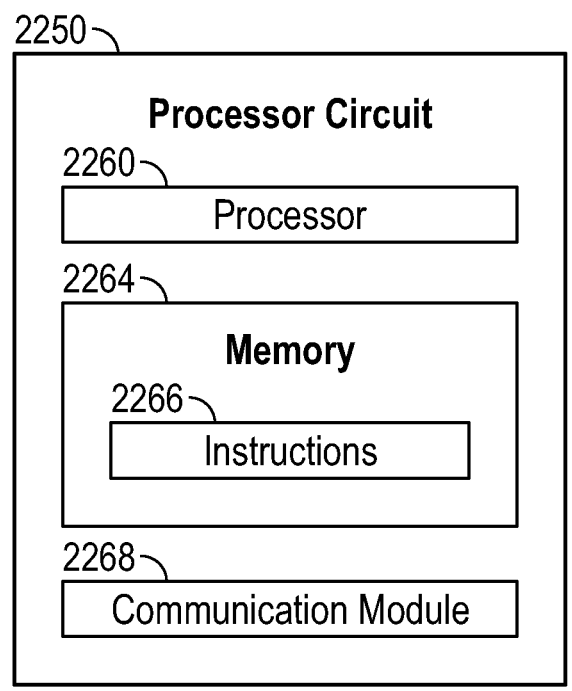
FIG. 22 is a schematic diagram of a processor circuit, according to embodiments of the present disclosure.

FIG. 22 is a schematic diagram of a processor circuit 2250, according to embodiments of the present disclosure. The processor circuit 2250 may be implemented in the ultrasound imaging system 100, or other devices or workstations (e.g., third-party workstations, network routers, etc.), or on a cloud processor or other remote processing unit, as necessary to implement the method. As shown, the processor circuit 2250 may include a processor 2260, a memory 2264, and a communication module 2268. These elements may be in direct or indirect communication with each other, for example via one or more buses.

The processor 2260 may include a central processing unit (CPU), a digital signal processor (DSP), an ASIC, a controller, or any combination of general-purpose computing devices, reduced instruction set computing (RISC) devices, application-specific integrated circuits (ASICs), field programmable gate arrays (FPGAs), or other related logic devices, including mechanical and quantum computers. The processor 2260 may also comprise another hardware device, a firmware device, or any combination thereof configured to perform the operations described herein. The processor 2260 may also be implemented as a combination of computing devices, e.g., a combination of a DSP and a microprocessor, a plurality of microprocessors, one or more microprocessors in conjunction with a DSP core, or any other such configuration.

The memory 2264 may include a cache memory (e.g., a cache memory of the processor 2260), random access memory (RAM), magnetoresistive RAM (MRAM), read-only memory (ROM), programmable read-only memory (PROM), erasable programmable read only memory (EPROM), electrically erasable programmable read only memory (EEPROM), flash memory, solid state memory device, hard disk drives, other forms of volatile and non-volatile memory, or a combination of different types of memory. In an embodiment, the memory 2264 includes a non-transitory computer-readable medium. The memory 2264 may store instructions 2266. The instructions 2266 may include instructions that, when executed by the processor 2260, cause the processor 2260 to perform the operations described herein. Instructions 2266 may also be referred to as code. The terms "instructions" and "code" should be interpreted broadly to include any type of computer-readable statement(s). For example, the terms "instructions" and "code" may refer to one or more programs, routines, sub-routines, functions, procedures, etc. "Instructions" and "code" may include a single computer-readable statement or many computer-readable statements.

The communication module 2268 can include any electronic circuitry and/or logic circuitry to facilitate direct or indirect communication of data between the processor circuit 2250, and other processors or devices. In that regard, the communication module 2268 can be an input/output (I/O) device. In some instances, the communication module 2268 facilitates direct or indirect communication between various elements of the processor circuit 2250 and/or the ultrasound imaging system 100. The communication module 2268 may communicate within the processor circuit 2250 through numerous methods or protocols. Serial communication protocols may include but are not limited to United States Serial Protocol Interface (US SPI), Inter-Integrated Circuit (I$^2$C), Recommended Standard 232 (RS-232), RS-485, Controller Area Network (CAN), Ethernet, Aeronautical Radio, Incorporated 429 (ARINC 429), MODBUS, Military Standard 1553 (MTh-STD-1553), or any other suitable method or protocol. Parallel protocols include but are not limited to Industry Standard Architecture (ISA), Advanced Technology Attachment (ATA), Small Computer System Interface (SCSI), Peripheral Component Interconnect (PCI), Institute of Electrical and Electronics Engineers 488 (IEEE-488), IEEE-1284, and other suitable protocols. Where appropriate, serial and parallel communications may be bridged by a Universal Asynchronous Receiver Transmitter (DART), Universal Synchronous Receiver Transmitter (USART), or other appropriate subsystem.

External communication (including but not limited to software updates, firmware updates, preset sharing between the processor and central server, or readings from the ultrasound device) may be accomplished using any suitable wireless or wired communication technology, such as a cable interface such as a USB, micro USB, Lightning, or FireWire interface, Bluetooth, Wi-Fi, ZigBee, Li-Fi, or cellular data connections such as 2G/GSM, 3G/UMTS, 4G/LTE/WiMax, or 5G. For example, a Bluetooth Low Energy (BLE) radio can be used to establish connectivity with a cloud service, for transmission of data, and for receipt of software patches. The controller may be configured to communicate with a remote server, or a local device such as a laptop, tablet, or handheld device, or may include a display capable of showing status variables and other information. Information may also be transferred on physical media such as a USB flash drive or memory stick.

A number of variations are possible on the examples and embodiments described above. For example, the pullback speed management system may be employed in anatomical systems within the body other than those described, or may be employed to image other disease types, object types, or procedure types than those described. The technology described herein may be applied to intraluminal imaging sensors of diverse types, whether currently in existence or hereinafter developed.

Accordingly, the logical operations making up the embodiments of the technology described herein are referred to variously as operations, steps, objects, elements, components, or modules. Furthermore, it should be understood that these may be performed in any order, unless explicitly claimed otherwise or a specific order is inherently necessitated by the claim language. All directional references e.g., upper, lower, inner, outer, upward, downward, left, right, lateral, front, back, top, bottom, above, below, vertical, horizontal, clockwise, counterclockwise, proximal, and distal are only used for identification purposes to aid the reader's understanding of the claimed subject matter, and do not create limitations, particularly as to the position, orientation, or use of the pullback speed management system. Connection references, e.g., attached, coupled, connected, and joined are to be construed broadly and may include intermediate members between a collection of elements and relative movement between elements unless otherwise indicated. As such, connection references do not necessarily imply that two elements are directly connected and in fixed relation to each other. The term "or" shall be interpreted to mean "and/or" rather than "exclusive or." Unless otherwise noted in the claims, stated values shall be interpreted as illustrative only and shall not be taken to be limiting.

The above specification, examples and data provide a complete description of the structure and use of exemplary embodiments of the pullback speed management system as defined in the claims. Although various embodiments of the claimed subject matter have been described above with a certain degree of particularity, or with reference to one or more individual embodiments, those skilled in the art could make numerous alterations to the disclosed embodiments without departing from the spirit or scope of the claimed subject matter. Still other embodiments are contemplated. It is intended that all matter contained in the above description and shown in the accompanying drawings shall be interpreted as illustrative only of particular embodiments and not limiting. Changes in detail or structure may be made without departing from the basic elements of the subject matter as defined in the following claims.

What is claimed is:

1. An intraluminal imaging system, comprising:
   an intraluminal imaging catheter comprising an imaging sensor disposed at a single location along a length of the intraluminal imaging catheter; and
   a processor circuit configured for communication with the intraluminal imaging catheter, wherein the processor circuit is configured to:
      control the imaging sensor to obtain a plurality of intraluminal images during manual movement of the intraluminal imaging catheter by a user through a body lumen of a patient, wherein the plurality of intraluminal images comprises a first intraluminal image obtained by the imaging sensor and a second intraluminal image obtained by the imaging sensor;
      perform image processing to identify an anatomical feature in the first intraluminal image and in the second intraluminal image;
      determine, based on the image processing, a change in a visual appearance of the anatomical feature between the first intraluminal image and the second intraluminal image, wherein the change in the visual appearance of the anatomical feature corresponds to:
         the first intraluminal image being obtained by the imaging sensor at a first position within the body lumen during the manual movement of the intraluminal imaging catheter by the user; and
         the second intraluminal image being obtained by the imaging sensor at a different, second position within the body lumen during the manual movement of the intraluminal imaging catheter by the user;
      determine, in real time during the manual movement of the intraluminal imaging catheter by the user, a longitudinal translation speed of the intraluminal imaging catheter using the plurality of intraluminal images obtained by the imaging sensor, wherein the determination of the longitudinal translation speed is based on:
         the change in the visual appearance of the anatomical feature between the first intraluminal image and the second intraluminal image; and
         a known time interval between the first intraluminal image and the second intraluminal image; and
      output, to a display in communication with the processor circuit, a screen display to the user, wherein the screen display includes a speed indicator based on the longitudinal translation speed.

2. The system of claim 1, wherein the processor circuit is configured to:
   update the longitudinal translation speed based on a third intraluminal image obtained while the intraluminal imaging catheter is moved through the body lumen; and
   dynamically modify the speed indicator in the screen display such that the speed indicator indicates the longitudinal translation speed based on the third intraluminal image.

3. The system of claim 1, wherein the processor circuit is further configured to output, via the screen display, an intraluminal image of the plurality of intraluminal images, wherein the intraluminal image is proximate to the speed indicator.

4. The system of claim 1, wherein the processor circuit is configured to determine the longitudinal translation speed without tracking a position of the intraluminal imaging catheter.

5. The system of claim 1, wherein the speed indicator comprises:
   a shape representative of a range of longitudinal translation speeds; and
   a marker positioned within the shape and representative of the determined longitudinal translation speed.

6. The system of claim 5, wherein the speed indicator comprises:
a region of the shape identifying an ideal range for the longitudinal translation speed, wherein the region extends from a first portion representative of a minimum translation speed to an opposite, second portion representative of a maximum translation speed.

7. The system of claim 1, wherein the processor circuit is configured to:
determine at least one of:
a length estimate of the body lumen based on the longitudinal translation speed; or
a volume estimate of the body lumen based on the longitudinal translation speed and an area of the body lumen in the plurality of intraluminal images; and
output at least one of the length estimate or the volume estimate via the screen display.

8. The system of claim 1, wherein the screen display further comprises a stylized diagram of the body lumen.

9. The system of claim 8, wherein the screen display further comprises a position of the intraluminal imaging catheter within the stylized diagram.

10. The system of claim 8, wherein the screen display further comprises a trail indicating past positions of the intraluminal imaging catheter.

11. The system of claim 10, wherein the trail is color coded in the screen display to indicate past longitudinal translation speeds of the intraluminal imaging catheter.

12. An intraluminal imaging method, comprising:
controlling, with a processor circuit in communication with an intraluminal imaging catheter, an imaging sensor of the intraluminal imaging catheter to obtain a plurality of intraluminal images during manual movement of the intraluminal imaging catheter by a user through a body lumen of a patient, wherein the plurality of intraluminal images comprises a first intraluminal image obtained by the single imaging sensor and a second intraluminal image obtained by the single imaging sensor, wherein the imaging sensor is disposed at a single location along a length of the intraluminal imaging catheter;
performing, with the processor circuit, image processing to identify an anatomical feature in the first intraluminal image and in the second intraluminal image;
determining, based on the image processing, a change in a visual appearance of the anatomical feature between the first intraluminal image and the second intraluminal image, wherein the change in the visual appearance of the anatomical feature corresponds to:
the first intraluminal image being obtained by the imaging sensor at a first position within the body lumen during the manual movement of the intraluminal imaging catheter by the user; and
the second intraluminal image being obtained by the imaging sensor at a different, second position within the body lumen during the manual movement of the intraluminal imaging catheter by the user;
determining, with the processor circuit, a longitudinal translation speed of the intraluminal imaging catheter in real time during the manual movement of the intraluminal imaging catheter by the user using the plurality of intraluminal images obtained by the imaging sensor, wherein determining the longitudinal translation speed is based on:
the change the visual appearance of the anatomical feature between the first intraluminal image and the second intraluminal image; and
a known time interval between the first intraluminal image and the second intraluminal image; and
outputting, to a display in communication with the processor circuit, a screen display to a user, wherein the screen display includes a speed indicator based on the longitudinal translation speed.

13. The system of claim 1,
wherein the intraluminal imaging catheter comprises an intravascular imaging catheter,
wherein the plurality of intraluminal images comprises a plurality of intravascular images,
wherein the body lumen comprises a blood vessel,
wherein the first intraluminal image and the second intraluminal image respectively comprise a first intravascular image and a second intravascular image.

14. The system of claim 13,
wherein the intravascular imaging catheter comprises an intravascular ultrasound (IVUS) imaging catheter,
wherein the plurality of intravascular images comprises a plurality of IVUS images, and
wherein the first intravascular image and the second intravascular image respectively comprise a first IVUS image and a second IVUS image.

15. The system of claim 1,
wherein the intraluminal imaging catheter comprises an intraluminal ultrasound imaging catheter,
wherein the plurality of intraluminal images comprises a plurality of intraluminal ultrasound images.

16. The system of claim 1, wherein the imaging sensor comprises a single array of imaging elements longitudinally co-located at the single location along the length of the intraluminal imaging catheter.

17. The system of claim 1, wherein the imaging sensor comprises an ultrasound transducer array.

18. The system of claim 1, wherein the imaging sensor comprises an optical coherence tomography (OCT) sensor.

19. An intravascular imaging system, comprising:
an intravascular imaging catheter comprising an imaging sensor disposed at a single location along a length of the intravascular imaging catheter; and
a processor circuit configured for communication with the intravascular imaging catheter, wherein the processor circuit is configured to:
control the imaging sensor to obtain a plurality of intravascular images during manual movement of the intravascular imaging catheter by a user through a blood vessel of a patient, wherein the plurality of intravascular images comprises a first intravascular image obtained by the single imaging sensor and a second intravascular image obtained by the single imaging sensor;
perform image processing to identify an anatomical feature in the first intravascular image and in the second intravascular image;
determine, based on the image processing, a change in a visual appearance of the anatomical feature between the first intravascular image and the second intravascular image, wherein the change in the visual appearance of the anatomical feature corresponds to:
the first intravascular image being obtained by the imaging sensor at a first position within the blood vessel during the manual movement of the intravascular imaging catheter by the user; and the second intravascular image being obtained by the imaging sensor at a different, second position within the blood vessel during the manual movement of the intravascular imaging catheter by the user;

determine, in real time during the manual movement of the intravascular imaging catheter by the user, a longitudinal translation speed of the intravascular imaging catheter using the plurality of intravascular images obtained by the imaging sensor, wherein the determination of the longitudinal translation speed is based on:

the change in the visual appearance of the anatomical feature between the first intravascular image and the second intravascular image; and a known time interval between the first intravascular image and the second intravascular image; and output, to a display in communication with the processor circuit, a screen display to the user, wherein the screen display includes a speed indicator based on the longitudinal translation speed.

20. The system of claim 19, wherein the blood vessel comprises peripheral vasculature.

21. The system of claim 19, wherein the blood vessel comprises cardiac vasculature.

22. The system of claim 19, wherein the imaging sensor comprises an ultrasound transducer array.

23. The system of claim 19, wherein the imaging sensor comprises an optical coherence tomography (OCT) sensor.

24. The system of claim 19, wherein the visual appearance of the anatomical feature comprises at least one of a shape of the blood vessel, a position of the blood vessel, a size of the blood vessel, or a branching vessel.

* * * * *